(12) United States Patent
Chatterjee et al.

(10) Patent No.: US 7,265,206 B2
(45) Date of Patent: *Sep. 4, 2007

(54) METHODS OF PRODUCTION OF PROTEINS

(75) Inventors: Deb K. Chatterjee, North Potomac, MD (US); Mary C. Longo, Germantown, MD (US); Elizabeth Flynn, Columbia, MD (US); Robert W. Oberfelder, Woodland, TX (US)

(73) Assignee: Invitrogen Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/329,418

(22) Filed: Jan. 11, 2006

(65) Prior Publication Data

US 2006/0269992 A1 Nov. 30, 2006

Related U.S. Application Data

(63) Continuation of application No. 10/728,766, filed on Dec. 8, 2003, which is a continuation of application No. 09/004,068, filed on Jan. 8, 1998, now Pat. No. 6,703,484.

(60) Provisional application No. 60/034,658, filed on Jan. 8, 1997.

(51) Int. Cl.
  *C07K 1/00* (2006.01)
  *C12P 21/06* (2006.01)
  *C12P 21/04* (2006.01)
(52) U.S. Cl. ............... 530/350; 435/69.1; 435/68.1
(58) Field of Classification Search ............... 530/350; 435/69.1, 68.1, 69.7

See application file for complete search history.

(56) References Cited

U.S. PATENT DOCUMENTS 4,405,720 A 9/1983 Merril (Continued)

FOREIGN PATENT DOCUMENTS

JP 01-503117 10/1989

(Continued)

OTHER PUBLICATIONS

Allen, R.C., and Budowle, B., "Component Visualization," in *Gel Electrophoresis of Proteins and Nucleic Acids*, Walter De Gruyter, Berlin, Germany, pp. 204-272 (1994).

(Continued)

*Primary Examiner*—Maryam Monshipouri
(74) *Attorney, Agent, or Firm*—Invitrogen Corporation; Emanuel Vacchiano

(57) ABSTRACT

The current invention provides methods for producing a polypeptide as inclusion bodies in bacterial host cells. The present methods are carried out by forming a gene construct comprising the genetic sequence encoding a polypeptide operatively linked to that of an inclusion partner protein, such as *E. coli* thioredoxin or a modified *E. coli* thioredoxin, such that host cells comprising the gene construct produce the polypeptide as intracellular inclusion bodies. The methods of the present invention facilitate the rapid isolation and purification of recombinant proteins. In addition, the present methods may be useful for producing polypeptides or proteins which are small and are typically difficult to express, as well as those proteins that are toxic to host cells such as *E. coli*. The present invention also provides plasmids, vectors and host cells to be used in the present invention for production of polypeptides, and methods of production of polypeptides using these vectors and host cells. The invention further provides methods for producing protein molecular weight ladders for use in protein gel electrophoresis, as well as proteins and protein molecular weight ladders produced by these methods.

41 Claims, 9 Drawing Sheets

```
CTCGGGTACAACACTGACAATAAAGAGTACGTTCTTGTTAAACTTA
AGGGTTTTTCTTCTGAAGATAAAGGCGAGTGGAAACTGAAACTCGA
TAATGCGGGTAAC GGTCAAGCAGTAATTCGTTTTCTTCCGTCTAAA
AATGATGAACAAGCACCATTCGCAATTCTTGTAAATCACGGTTTCA
AGAAAAATGGTAAATGGTATATTGAAACATCATCTACCCATGATT
ACGATTCTCCAGTACAATACATCAGTAAAAATGATCTCGGG
```

(SEQ ID NO:1)

U.S. PATENT DOCUMENTS

| | | | |
|---|---|---|---|
| 4,468,466 | A | 8/1984 | Morrissey |
| 4,507,233 | A | 3/1985 | Saito et al. |
| 4,575,452 | A | 3/1986 | Lee et al. |
| 4,677,196 | A | 6/1987 | Rausch et al. |
| 4,766,224 | A | 8/1988 | Rausch |
| 4,782,027 | A | 11/1988 | Lee et al. |
| 4,920,059 | A | 4/1990 | Moeremans et al. |
| 5,132,439 | A | 7/1992 | Shultz et al. |
| 5,270,181 | A | 12/1993 | McCoy et al. |
| 5,273,906 | A | 12/1993 | Shultz et al. |
| 5,279,792 | A | 1/1994 | Moeremans et al. |
| 5,292,646 | A | 3/1994 | McCoy et al. |
| 5,330,902 | A | 7/1994 | Keck et al. |
| 5,449,758 | A | 9/1995 | Hartley |
| 5,605,691 | A | 2/1997 | Carroll |
| 5,616,502 | A | 4/1997 | Haugland et al. |
| 5,705,649 | A | 1/1998 | Shultz et al. |

FOREIGN PATENT DOCUMENTS

| | | |
|---|---|---|
| JP | 05-507209 | 10/1993 |
| JP | 08-509504 | 10/1996 |
| WO | WO-88/07086 | 9/1988 |
| WO | WO92/01707 | 2/1992 |
| WO | WO-92/13955 | 8/1992 |
| WO | WO-95/19993 | 7/1995 |
| WO | WO-96/08570 | 3/1996 |
| WO | WO96/17942 | 6/1996 |
| WO | WO-96/30514 | 10/1996 |
| WO | WO97/28248 | 8/1997 |

OTHER PUBLICATIONS

Ausubel, F.M., et al., "Protein Expression," in *Current Protocols in Molecular Biology*, vol. 2, John Wiley & Sons, Inc., Hoboken, NJ, pp. 16.4.1-16.8.14 (1994).

Barger, B.O., et al., "Estimation of Molecular Weight by Polyacrylamide Gel Electrophoresis Using Heat Stable Fluorophors," *Anal. Biochem.* 70:327-335, Academic Press (1976).

Betton, J-M., and Hofnung, M., "Folding of a Mutant Maltose-binding Protein of *Escherichia coli* Which Forms Inclusion Bodies," *J. Biol. Chem.* 271:8046-8052, American Society for Biochemistry and Molecular Biology (1996).

Biorad, "Electrophoresis and Blotting Standards. Protein Standards," *Life Science Research Products, Price List S*, p. 316, (1993).

Bosshard, H.F., and Datyner, A., "The Use of a New Reactive Dye for Quantitation of Prestained Proteins on Polyacrylamide Gels," *Anal. Biochem.* 82:327-333. Academic Press (1977).

Buchner, J., and Rudolph, R., "Renaturation, Purification and Characterization of Recombinant $F_*$-Fragments Produced in *Escherichia coli*," *Biotechnology* 9.157-162. Nature Pub. Co. (1991).

Carter, P., "Site-Specific Proteolysis of Fusion Proteins," in *Protein Purification: From Molecular Mechanisms to Large-Scale Processes*, American Chemical Society Symposium Series, vol. 427, Ladisch, M.R., et al., eds., American Chemical Society, Washington, DC. pp. 181-193 (1990).

Chatterjee, D.K., et al., "Cloning and overexpression of the gene encoding bacteriophage T5 DNA polymerase," *Gene* 97:13-19, Elsevier Science (1991).

Chatterjee, D.K., et al., "Genetic organization of the *Kpn*1 restriction-modification system," *Nucl Acids Res.* 19:6505-6509, Oxford University Press (1991).

Coburn, G.A., and Mackie, G.A., "Overexpression, Purification, and Properties of *Escherichia coli* Ribonuclease II," *J. Biol. Chem.* 271:1048-1053, American Society for Biochemistry and Molecular Biology (1996).

Dalmia, B.K., et al., "Domain E of *Bacillus macerans* Cyclodextrin Glucanotransferase: An Independent Starch-Binding Domain," *Biotechnol. Bioeng.* 47:575-584, Wiley Interscience (1995).

Datyner, A., and Finnimore, E.D., "A Prestaining Method for the Quantitative Assay of Proteins on Polyacrylamide Gels," *Anal. Biochem.* 55:479-491, Academic Press (1973).

Dekker, N., et al., "In vitro folding of *Escherichia coli* outer-membrane phospholipase A," *Eur. J. Biochem.* 232:214-219, Blackwell Science (1995).

Derman, A.I., and Beckwith, J., "*Escherichia coli* Alkaline Phosphatase Localized to the Cytoplasm Slowly Acquires Enzymatic Activity in Cells Whose Growth Has Been Suspended: a Caution for Gene Fusion Studies," *J. Bacteriol.* 177:3764-3770, American Society for Microbiology (1995).

Flynn, E., et al., "Protein Analysis with the BenchMark™ Protein Ladders," *Focus* 19:33-35, Life Technologies (1997).

Georgiou, G., et al., "Localization of Inclusion Bodies in *Escherichia coli* Overproducing β-Lactamase or Alkaline Phosphatase," *Appl. Environ. Microbiol.* 52:1157-1161, American Society for Microbiology (1986).

Griffith, I.P., "Immediate Visualization of Proteins in Dodecyl Sulfate-Polyacrylamide Gels by Prestaining with Remazol Dyes," *Anal. Biochem.* 46:402-412, Academic Press (1972).

Haugland, R., "Handbook of Fluorescent Probes and Research Chemicals. Section 1.5, Dyes with Absorption Maxims Between 500 and 540 nm," pp. 25-29, Molecular Probes Inc., available at: http://web.archive.org/web/19970607210142/www.probes.com/acrobat/ch01-5.pdf.

Haugland, R, "Handbook of Fluorescent Probes and Research Chemicals, Section 1.6, Long-Wavelength Dyes," pp. 29-35, Molecular Probes Inc., available at: http://web.archive.org/web/19970607210142/www.probes.com/acrobat/ch01-6.pdf.

Hitorni, Y., et al., "High Efficiency Prokaryotic Expression and Purification of a Portion of the Hepatitis C Core Protein and Analysis of the Immune Response to Recombinant Protein in BALB/c Mice," *Virol. Immunol.* 8:109-119, Mary Ann Liebert Inc. (1995).

Hochuli, E., and Piesecki, S., "Interaction of Hexahistidine Fusion Proteins with Nitrilotriacetic Acid-Chelated $Ni^{2+}$ Ions," *METHODS: A Companion to Methods in Enzymology* 4:68-72, Academic Press (1992).

Höög, J-O., et al., "Nucleotide sequence of the thioredoxin gene from *Escherichia coli*," *Biosci. Rep.* 4:917-923, The Biochemical Society (1984).

Kim, S-O., and Loe, Y.I., "High-level expression and simple purification of recombinant human insulin-like growth factor I," *J. Biotechnol* 48:97-105, Elsevier Science (1996).

Kuheli, R., et al., "The preparation of catalytically active human cathepsin B from its precursor expressed in *Escherichia coli* in the form of inclusion bodies," *Eur. J. Biochem.* 229:533-539, Blackwell Science (1995).

LaVallie, E.R., et al., "A Thioredoxin Gene Fusion Expression System That Circumvents Inclusion Body Formation in the *E. coli* Cytoplasm," *Biotechnology* 11:187-193, Nature Pub. Co. (1993).

Lunn, C.A., et al., "Amplification and Purification of Plasmid-encoded Thioredoxin from *Escherichia coli* K12," *J. Biol. Chem.* 259:10469-10474, American Society of Biological Chemists Inc. (1984).

Magin, T.M., et al., "Analysis of cytokeratin domains by cloning and expression of intact and deleted polypeptides in *Escherichia coli*," *EMBO J.* 6:2607-2615, IRL Press Ltd. (1987).

Molecular Probes, "Conjugation with Amine-Reactive Probes," Product Information Sheet MP0143, p. 1-8 (1996).

Molecular Probes Catolg, "Handbook of Fluorescent Probes and Research Chemicals," 6th Edition, pp. 9-10 (1996).

Neophytou, P.I. et al., "Development of a procedure for the direct cloning of T-cell epitopes using bacterial expression systems," *J. Immunol. Methods* 196:63-72, Elsevier Science (1996).

Oberfelder, R.W., et al., "Protein Expression by Inclusion," *FASEB J.* 11:A1200, Abstract No. 2007, Federation of American Societies for Experimental Biology (Jul./Aug. 1997).

Oeda, K., et al., "Formation of Crystals of the Insecticidal Proteins of *Bacillus thuringiensis* subsp. aizawai IPL7 in *Escherichio coli*," *J. Bacteriol.* 171:3568-3571, American Society for Microbiology (1989).

Rinas, U., and Bailey, J.E., "Overexpression of Bacterial Hemoglobin Causes Incorporation of Pre-β- Lactamase into Cytoplasmic Inclusion Bodies," *Appl., Environ. Microbiol.* 59:561-566, American Society for Microbiology (1993).

Sambrook, J., et al., "Expression of Cloned Genes in *Escherichia coli*," in *Molecular Cloning: A Laboratory Manual. Second Edition*, Cold Spring Harbor Laboratory Press, Cold Spring Harbor, N.Y. pp. 17.2-17.9 (1989).

Schneider, E., et al., "Functional Purification of Bacterial ATP-Binding Cassette Transporter Protein (MalK) from the Cytoplasmic Fraction of an Overproducing Strain," *Protein Expr. Purif.* 6:10-14, Academic Press (1995).

Sigma Deutschland "Electophoresis Reagents," *Biochemikalien Organische Verbindungen und Diagnostike Produktkatalog*, Diesenhoffen, Germany, pp. 1898-1902 (1996).

Tokatlidis, K., et al., "High activity of inclusion bodies formed in *Escherichia coli* overproducing *Clostridium thermocellum* endoglucanase D," *FEBS Lett.* 282:205-208, Elsevier Science (1991).

Toone, W.M. et al., "*dead*, a New *Escherichia coli* Encoding a Presumed ATP-Dependent RNA Helicase. Can Suppress a Mutation in *rpsB*, the Gene Encoding Ribosomal Protein S2," *J. Bacteriol* 173:329-3302, American Society for Microbiology (1991).

Vandenbroeck, K., et al., "Refolding and single-step purification of porcine interferon-γ from *Escherichia coli* inclusion bodies. Conditions for reconstitution of dimeric IFN-γ, " *Eur. J. Biochem.* 215:481-486, Blackwell Scientific (1963).

Wei, G., and Tang, J-G., "Formation of Inclusion Bodies May Be the Key Factor for the Stability of Expressed Products in *E. coli*," *Biochem. Mol. Biol. Intl.* 37:895-901, Acedemic Press (1995).

Wannacker, E-L., "Directed Mutagenesis," in *From Genes to Clones: Introduction to Gene Technology*, VCH, Weinheim, Germany, pp. 451-481 (1987).

Yasufuku, K., et al., "High-Yield Production of Recombinant Endothelin-l," *J. Biochem.* (Tokyo) 112:360-365, Oxford University Press (1992).

Supplementary European Search Report for Patent Application No. EP 98 90 3438, Search Completed Apr. 20, 2004, European Patent Office, Munich, Germany.

Asermely et al. "Identification of a recombinant synaptobrevin-thioredoxin fusion protein by capillary zone electrophoresis using laser-induced fluorescence detection" Journal of Chromatography B, 695:67-75 (1997).

Reischl, Udo, et al., "Preparative SDS-Page Electrophoresis of a Recombinant Epstein-Barr Virus Encoded Protein and Its Application in Serodiagnostic Test Systems", *Bio-Rad Laboratories, Inc., Bulletin 2024*, (2002), 1-4.

CTCGGGTACAACACTGACAATAAAGAGTACGTTCTTGTTAAACTTA
AGGGTTTTTCTTCTGAAGATAAAGGCGAGTGGAAACTGAAACTCGA
TAATGCGGGTAAC GGTCAAGCAGTAATTCGTTTTCTTCCGTCTAAA
AATGATGAACAAGCACCATTCGCAATTCTTGTAAATCACGGTTTCA
AGAAAAATGGTAAATGGTATATTGAAACATCATCTACCCATGATT
ACGATTCTCCAGTACAATACATCAGTAAAAATGATCTCGGG (SEQ ID NO:1)

FIG. 1

CCATGGGTTTTTCTTCTGAAGATAAAGGCGAGTGGAAACTGAAACT
CGATAATGCGGGTAACGGTCAAGCAGTAATTCGTTTTCTTCCGTCTA
AAAATGATGAACA AGCACCATTCGCAATTCTTGTAAATCACGGTTTC
AAGAAAAATGCTAAATGGTATATTGAAACATCATCTACCCATGATT
ACGATTCTCCAGTACAATACATCAGTAAAAATGATCTCGGGTACAAC
ACTGACAATAAACACCACCACCACCACCAC (SEQ ID NO:2)

FIG. 2

CATATGAGCGATAAAATTATTCACCTGACTGACGACAGTTTTGACAC
GGATGTACTCAAAGCGGACGGGGCGATCCTCGTCGATTTCTAGAGTG
GTGCGGTCCGTGCAAAATGATCGCCCCGATTCTGGATGAAATCGCT
GACGAATATCAGGGCAAACTGACCGTTGCAAAACTGAACATCGATC
AAAACCCTGCTCACTGCGCCGAAATATGGCATCCGTGGTATCCCG
ACTCTGCTGCTGTTCAAAAACGGTGAACACCACCACCACCACCAC (SEQ ID NO:5)

FIG. 3

CCATGCTCATATGAGCGATAAAATTATTCACCTGACTGACGACAGTT
TTGACACGGATGTACTCAAAGCGGACGGGGCGATCCTCGTCGATTTC
TGGGCAGAGTGGTGCGGTCCGTGCAAAATGATCGCCCCGATTCTGGA
TGAAATCGCTGACGAATA TCAGGGCAAACTGACCGTTGCAAAACTG
AACATCGATCAAAACCCTGGCACTG CGCCGAAATATGGCATCCGTGGT
GGACTCGGGTACAACACTGACAATAAACACCACCACCACCACCAC (SEQ ID NO:8)

FIG.4

CTCGGGAGCGATAAAATTATTCACCTGACTGACGACAGTTTTGACA
CGGATGTACTCAAAGCGGACGGGGCGATCCTCGTCGATTTCTGGGC
AGAGTGGTGCGGTCCGTGCAAAATGATCGCCCCGATTCTGGATGAA
ATCGCTGACGAATATCAGGG CAAACTGACCGTTGCAAAACTGAAC
ATCGATCAAAACCCTGGCACTGCGCCGAAATATGGCATCCGTGGTA
TCCCGACTCTGCTGCTGTTCAAAAACGGTGAAGTGGCGGCAACCAA
ACTCGGG (SEQ ID NO:11)

FIG.5

CTCGGGAAGCTGACTAATCCGGAAGTAGAACTGCCGAACGCAGAAC
TGCTAGGCAAACGCCGTCTGGAAAAATTCGCCGCTAAAGTACAGCA
GCAGCTGGAAAGCAGCGATCTGGATCAATACCGCGCACTGCTCGGG (SEQ ID NO:14)

FIG.6

CTCGGGGCACATAAAATGCTAAAAGATACAGGCATTATTGCTATCA
GCATTGATGACTATGAATTTGCTCATTTAAAAATACTGATGGATAA
AATTTTCGGTGAAGATAATTTCATCGGAAATATCGTCGTTTGTCGT
TCAAAAAATGGAAAAGTGAGC AAGCGAAATATAGCGTCTGCTCAT
GAATATTTACTGGTTTATGGAAAATCAGATATGGCGGAACTATCTG
GACAACCAGATGATAAATCTCTTTATGATAAAGTTGATTGTTTTGG
TGAATATAGAATTGACGGAATGTTCAGAAAAAAGGTGATTCAAG
TTTGAGAACTGATCGCCCTAATATGTTTTATCCTTTATATTTTAACC
CATCAACAGGTGAAGTACAGGTAGAGCCAGAACTCGGG (SEQ ID NO:17)

FIG.7

1 2 3 4 5 6 M 7 8 9 10 11 12 13 14 pH: 7.2 8.2 9.2 7.2 8.2 9.2 M 7.2 8.2 9.2 7.2 8.2 9.2 9.2 8.7
Lane: 1 2 3 4 5 6 M 7 8 9 10 11 12 13 14

1  2  3  M  4  5  6  7  8  9  10  11  12  13  14 pH:  7.2 8.2 9.2  M  7.2 8.2 9.2  7.2 8.2 9.2  7.2 8.2 9.2  8.2 9.7
Lane: 1  2  3  M  4  5  6  7  8  9  10  11  12  13  14

METHODS OF PRODUCTION OF PROTEINS

CROSS REFERENCE TO RELATED APPLICATIONS

This application is a continuation of U.S. application Ser. No. 10/728,766, filed Dec. 8, 2003, pending which is a continuation of U.S. application Ser. No. 09/004,068, filed Jan. 8, 1998, now U.S. Pat. No. 6,703,484, which claims priority to U.S. Provisional Application No. 60/034,658, filed Jan. 8, 1997, the contents of each of which are entirely incorporated herein by reference.

BACKGROUND OF THE INVENTION

1. Field of the Invention

The present invention is in the fields of molecular biology and protein engineering. The invention is directed to methods for the production of recombinant proteins. More specifically, the invention is directed to methods for producing recombinant proteins as inclusion bodies in bacteria, particularly *Escherichia coli*. The present invention also provides plasmids, vectors and host cells to be used in the present invention for production of recombinant proteins, and methods of purification of the proteins produced by these methods. The invention is also directed to proteins produced by these methods. The invention is also directed to methods for production of protein molecular weight marker ladders, and to ladders produced by these methods.

2. Related Art

With the advent of recombinant DNA technology, it has become almost routine to produce large amounts of proteins in heterologous expression systems, such as transformed host cells, for commercial and basic research purposes. Among the expression host systems, *E. coli* is the most popular system because of ease with which *E. coli* can be manipulated. However, expression of heterologous proteins in host cells has some limitations. These include: inefficient translation of mRNA due to the presence of infrequently used codons (Kane, J., *Current Opin. Biotech* 6:494-500 (1995)), instability of mRNA in *E. coli* (Bachmair, A. et al., *Science* 234:179-186 (1986); Olins, P. & Lee, S., *Current Opin. Biotech* 6:501-506 (1993)), toxic effect of the protein being expressed (Brosius, J., *Gene* 27:161-172 (1984); Studier, W. & Mofatt, B., *J. Mol. Biol.* 189:113-130 (1986)), and formation of inclusion bodies because of inappropriate folding of the protein (Schein, C., *Bio/Technology* 7:1141-1149 (1989); Mitraki, A. & King, J., *Bio/Technology* 7:690-697 (1989)). To solve these problems, a variety of techniques have been developed.

Gene fusion is one of the most popular strategies to express proteins of interest. This particular technique is used to produce large amounts of heterologous protein by fusing the protein of interest to the carboxy terminal end of a fusion partner (LaVallie, E., and McCoy, J., *Curr. Opin. Biotech* 6:501-506). As an example of this approach, methods have been developed for selective isolation of a desired protein or polypeptide by constructing a recombinant vector containing a DNA sequence coding for the desired protein or polypeptide which is operatively linked to a DNA sequence coding for protein A (WO 84/03103). The expressed fusion protein is then selectively isolated by adsorption onto an IgG-supporting carrier, which binds protein A, followed by desorption of the fusion protein. The fusion protein is then cleaved at a unique cleavage site with a cleavage agent, which may include proteases, hydroxylamine, cyanogen bromide or formic acid, to give the purified protein.

Most systems used for the manufacture of recombinant polypeptides attempt to minimize the production of the polypeptide in inclusion bodies in the expressing host cells. One important reason for these attempts is that the production of polypeptides in inclusion bodies often yields a biochemically inactive, denatured, or otherwise functionally or structurally compromised polypeptide upon its release from the inclusion bodies via standard solubilization techniques. While a variety of methods have shown some promise in minimizing inclusion body formation, gene fusion techniques in particular have been utilized to produce soluble proteins which otherwise would have been produced as inclusion bodies.

However, the formation of inclusion bodies within host cells can also be advantageous. For example, inclusion bodies constitute highly dense and concentrated "packets" of the desired polypeptide, from which contaminating host cell proteins can be removed by methods as simple as centrifugation. After their isolation, controlled conversion of the inclusion bodies to a soluble form could provide a rich source of the desired polypeptide in its pure, biologically active or structurally intact form. The difficulty with such an approach, however, has been that it is usually nearly impossible to predict whether or not a recombinant polypeptide will form inclusion bodies when it is expressed in a host cell.

Thus, the current invention provides a system in which controlled formation of inclusion bodies is used to produce a desired polypeptide. By this controlled formation of inclusion bodies, purification of the desired polypeptide is rendered faster and more complete, and subsequent controlled solubilization of the inclusion bodies provides a high yield of pure polypeptide in its active form.

BRIEF SUMMARY OF THE INVENTION

The current invention provides a system wherein the genetic sequence encoding a first polypeptide is operatively linked or fused to that encoding an inclusion partner protein, such as thioredoxin or a modified thioredoxin, which is capable of forming inclusion bodies in a host cell upon expression. Specifically, the invention provides a method for producing a polypeptide in the form of inclusion bodies comprising (a) obtaining a host cell comprising a first nucleic acid molecule encoding a recombinant polypeptide operatively linked to a second nucleic acid molecule encoding an inclusion partner protein, thereby forming a gene fusion construct; and (b) cultivating the above host cell under conditions favoring production of the polypeptide as inclusion bodies in the host cell. The invention also provides the above method further comprising (c) isolating the inclusion bodies from the host cell; and (d) releasing the polypeptide from the inclusion bodies. According to the present invention, the first nucleic acid molecule encoding the polypeptide may be obtained from a prokaryotic cell, particularly a bacterial cell and most particularly an *Escherichia coli* cell, or from a eukaryotic cell, particularly an animal cell, a plant cell or a yeast cell, more particularly a mammalian animal cell, and most particularly a human cell, and the second nucleic acid molecule encoding the inclusion partner protein may be obtained from a bacterial cell, most preferably an *Escherichia coli* cell. The inclusion partner protein may be any protein that forms an inclusion body upon expression in a host cell, and is preferably a bacterial protein, more preferably a bacterial thioredoxin or modified bacterial thioredoxin, and most preferably a carboxy terminal-truncated form of *E. coli* thioredoxin. Preferably, the gene fusion construct is inserted into a vector prior to being introduced into the host cell. According to one aspect of the invention, the polypeptide of interest may be released from inclusion bodies, formed by the gene fusion construct, by cleavage with a chemical such as cyanogen bromide, or more preferably with an enzyme such as thrombin or enterokinase. According to another aspect, a nucleic acid sequence encoding a protein-specific cleavage site may be placed between the nucleic acid sequence encoding the inclusion partner protein and the recombinant polypeptide in the gene fusion construct; upon expression of the fusion protein as inclusion bodies in the host cells, the recombinant polypeptide may then be released therefrom by treating the inclusion bodies with an enzyme or other chemical that specifically recognizes and cleaves at the protein-specific cleavage site. The invention also provides the above-described methods wherein the gene fusion construct comprises plasmid pTrcprl-monomer, and provides plasmid pTrcprl-monomer. The invention is also directed to the above-described methods wherein the host cell is a bacterial cell, most preferably an *Escherichia coli* cell, and wherein the vector used is an expression vector, most preferably plasmids pTrc99A or pTrxfus. The invention also provides these vectors, and host cells, particularly bacterial cells and most particularly *Escherichia coli* cells, comprising these vectors. Although the present invention is most particularly directed to methods for the production of fragments of the gene 32 protein of bacteriophage T4, of KpnI methylase and Dead-Box protein, any recombinant polypeptide may be produced by the present methods. The invention also provides recombinant polypeptides produced by the above-described methods. Thus, the present system provides reliable methods for producing any heterologous protein as inclusion bodies in a host cell, thereby facilitating the rapid isolation and purification of recombinant proteins produced in bacterial host cells. In addition, the methods provided by the present invention may be used to produce polypeptides that are small or difficult to express, as well as those that are toxic to host cells such as *E. coli*.

The invention also provides methods for producing a protein molecular weight marker ladder, comprising (a) obtaining one or more nucleic acid molecules wherein each of the nucleic acid molecules encodes one or more polypeptides of different molecular weights of the molecular weight ladder; (b) transforming one or more host cells with one or more of the nucleic acid molecules; (c) culturing the host cells under conditions favoring the production of each of the polypeptides of the molecular weight ladder; and (d) isolating each of the polypeptides. The invention is particularly directed to such methods wherein at least one of the nucleic acid molecules encodes a plurality of the polypeptides of different molecular weights of the molecular weight ladder, and wherein the nucleic acid molecules each encode a different polypeptide of the molecular weight ladder. The invention is also directed to such methods wherein the host cell comprises a nucleic acid molecule encoding a plurality of polypeptides of the molecular weight ladder, and wherein each of the host cells comprises a different nucleic acid molecule each encoding a different polypeptide of the molecular weight ladder. The invention also provides such methods wherein a host cell comprises two or more of the nucleic acid molecules each encoding a different polypeptide of the molecular weight ladder, and wherein such method further comprises admixing each of the different polypeptides to form a molecular weight ladder. The present invention is particularly directed to such methods wherein the polypeptides of the molecular weight ladder are produced as inclusion bodies, and wherein the nucleic acid molecule encoding the polypeptide(s) is inserted into a vector, most preferably an expression vector, prior to transforming the host cells. Protein molecular weight ladders produced by the methods of the present invention are preferably prestained, and the invention provides optimal conditions for prestaining of the proteins to produce these molecular weight ladders. The present invention also provides protein molecular weight marker ladders, which are preferably prestained, produced by these methods.

The invention also generally relates to methods for producing a stained protein and more particularly prestained protein ladders. Such methods of the invention comprise contacting the one or more proteins or polypeptides of interest with one or more dyes under conditions sufficient to completely or substantially completely label or complex the dye(s) to the protein molecule(s). Preferably, he staining method of the invention is performed on the proteins or protein sample prior to size separation by, for example, gel electrophoresis. Thus, use of the protein or polypeptide staining method of the invention provides a homogeneous or near homogeneous sample in which all or substantially all of the proteins or polypeptides in the sample have been stained or complexed with the dye of interest. Such uniform staining provides increased color intensity upon examination of stained proteins due at least in part to more dye being complexed with the proteins or polypeptides (e.g., increased staining of the proteins of interest). Additionally, because of the uniformity and/or completeness of staining, the character of the stained protein will appear more consistent in subsequent analysis. Thus, when performing size analysis on the stained proteins or polypeptides of the invention, the proteins or polypeptides will be the same or substantially the same size. Such a feature of the stained proteins or polypeptides of the invention provides for superior protein molecular weight markers which allow more accurate size determination of an unknown protein or polypeptide.

The invention thus relates to a method of staining one or more polypeptides or proteins comprising:

(a) mixing or contacting a sample comprising the one or more polypeptides or proteins with one or more dyes; and (b) incubating the mixture under conditions sufficient to produce stained proteins or polypeptides having the same or substantially the same size. Such method may further comprise separating the stained proteins by size. Size separation may be accomplished by any known technique, including gel electrophoresis, capillary electrophoresis, gel filtration chromatography and the like.

The invention also relates to a method for staining one or more polypeptides or proteins comprising:

(a) mixing or contacting a sample comprising the one or more polypeptides or proteins with one or more dyes; and (b) incubating the mixture under conditions sufficient to produce stained proteins or polypeptides wherein substantially all of the proteins or polypeptides are complexed with the dye. Such methods may further comprise separating the stained proteins by size using standard techniques such as those described above.

Any conditions may be utilized to produce the desired result in accordance with the invention. In particular, protein concentrations, dye concentrations, pH, ionic conditions, temperature, and duration of exposure, or combinations of these parameters, may be varied to produce stained proteins or prestained molecular weight markers of the invention. In accordance with the invention, pH of the solution to which the protein(s) and dye(s) are added may be varied from about 7-12, incubation temperature may be varied between about 20° C.-80° C. (more preferably about 37° C.-70° C., and still more preferably about 50° C.-70° C.), and the duration of incubation may vary from about 1-200 hours (preferably about 2-200 hours, about 2-100 hours, about 6-100 hours, about 6-72 hours, about 6-48 hours, more preferably about 12-48 hours, and still more preferably about 12-24 hours).

Any one or a number of proteins or peptides may be stained in accordance with the invention. Such staining methods may be accomplished on different proteins (different size and/or type) at the same time or separately. If desired, separately stained proteins may be mixed after staining to provide a mixture of stained proteins having different sizes to produce, for example, a protein molecular weight ladder of the invention. Preferably, the molecular weight ladder of the invention comprises at least two and preferably at least three proteins of different sizes. More preferably, the ladders of the invention comprise 3-20, still more preferably 3-15, and still more preferably 3-10, proteins of different sizes.

The invention also relates to a method for sizing one or more proteins or polypeptides of unknown size or molecular weight, comprising:

(a) separating, according to size, the protein molecular weight ladder of the invention, and the one or more proteins or polypeptides of unknown size; and (b) determining the size and/or molecular weight of the protein(s) or polypeptide(s). Such determination may be made by comparison of the mobility of the unknown protein(s) or polypeptide(s) to that of the molecular weight ladder of the invention by standard techniques such as gel electrophoresis, capillary electrophoresis, etc.

The invention also provides for stained polypeptides and stained molecular weight markers produced in accordance with the methods of the invention and to kits containing them. Such kits comprise a carrier means, such as a box, carton, or the like, being compartmentalized to receive in close confinement therein one or more container means such as tubes, vials, ampules, bottles or the like, wherein a first container means comprises one or more stained polypeptides of the invention or one or more of the stained molecular weight marker ladders of the invention. In one such aspect of the invention, a number of individual containers may be provided in a kit, each container containing a different sized (and/or type) stained polypeptide, such that the end user may selectively prepare different molecular weight markers having a different combination of differently sized proteins. Thus, the invention provides the end user with flexibility in making an appropriate marker ladder depending on the need. Moreover, kits of the invention may also provide separate containers containing differently stained polypeptides (e.g., stained with different dyes), thus providing the end user with flexibility not only in varying the size or pattern of the molecular weight ladder but also the color or colors attributed to the individual peptides or bands in the ladder. The kits of the invention may further comprise one or more additional container means containing components which facilitate size analysis of proteins, such as acrylamide, SDS, gel or capillary electrophoresis reagents and/or equipment, and the like.

Other preferred embodiments of the present invention will be apparent to one of ordinary skill in light of the following drawings and description of the invention, and of the claims.

BRIEF DESCRIPTION OF THE DRAWINGS/FIGURES

FIG. 1 (SEQ ID NO:1) is a depiction of the 264-bp (gene32) AvaI fragment derived from pPrL2107 used to make multimers in pPrL2001.

FIG. 2 (SEQ ID NO:2) is a depiction of the 261-bp fragment with a single AvaI site used to prepare plasmid ptcprl-monomer.

FIG. 3 (SEQ ID NO:5) is a depiction of the delta thioredoxin sequence, plasmid pTrxfusprl10A, used to make the 10 kD protein.

FIG. 4 (SEQ ID NO:8) is a depiction of the trxA-concat sequence having NcoI and NdeI sites used to make concatamers. This plasmid, designated pTrxA-concat, served as the inclusion partner.

FIG. 5 (SEQ ID NO:11) is a depiction of the delta thioredoxin sequence used to make trxAtrxA concatamers.

FIG. 6 (SEQ ID NO:14) is a depiction of the 138-bp Dead-box fusion partner fragment used to make the molecular weight ladder by fusion with pTrxA-concat.

FIG. 7 (SEQ ID NO:17) is a depiction of the 15 kD KpnI methylase fusion partner fragment used to make the molecular weight ladder by fusion with pTrxA-concat.

Figure 9:
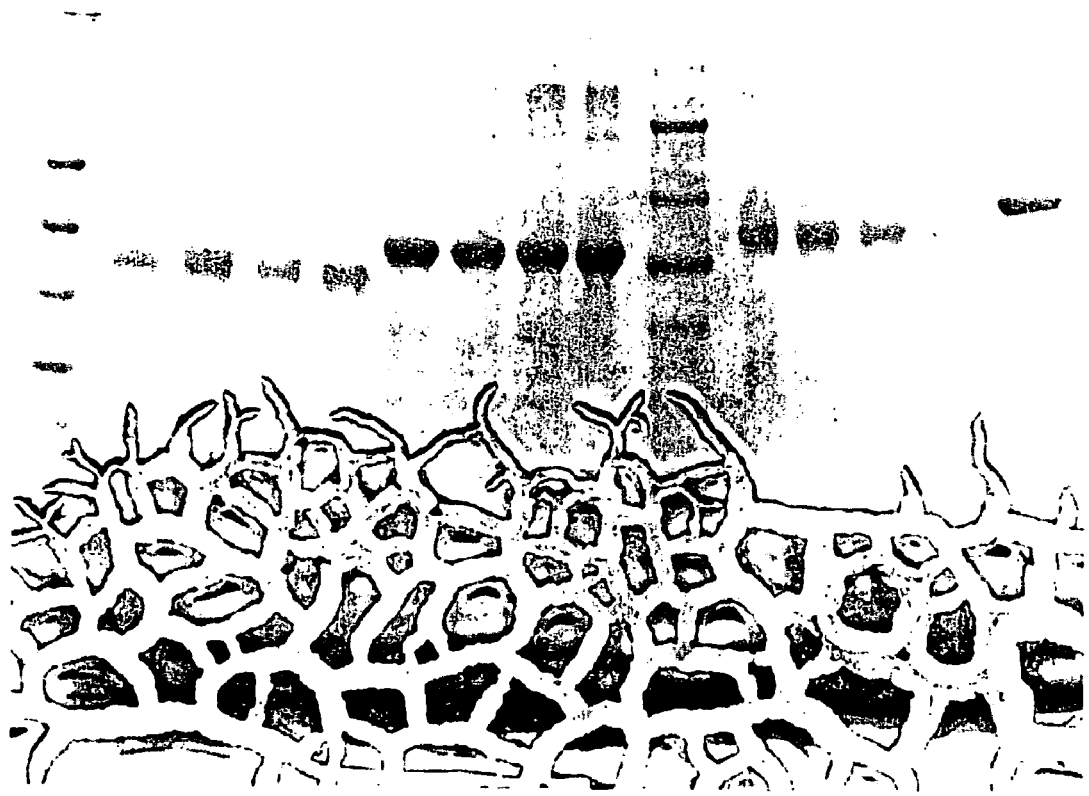

FIG. 9 is a photograph of a 4-20% SDS-PAGE gradient gel of 50 kD (lanes 1-8) and 60 kD (lanes 9-13) reference proteins prestained overnight with eosin isothiocyanate at room temperature (lanes 1-4 and 9-12) or at 50EC (lanes 5-8 and 13) at the indicated pHs. M: molecular weight standard ladders (two different preparations).

Figure 10:

FIG. 10 is a photograph of a 4-20% SDS-PAGE gradient gel of 40 kD (lanes 1-12) and 50 kD (lanes 13, 14) molecular weight markers prestained overnight with eosin isothiocyanate at room temperature (lanes 1-3,7-9) or at 50EC (lanes 4-6, 10-14) at the indicated pHs. M: molecular weight standard ladder.

Figure 11:

FIG. 11 is a photograph of a 4-20% SDS-PAGE gradient gel of 50 kD molecular weight markers prestained overnight with eosin isothiocyanate at room temperature (lanes 1-3,7-9) or at 50EC (lanes 4-6, 10-14) at the indicated pHs. M: molecular weight standard ladder.

Figure 12:
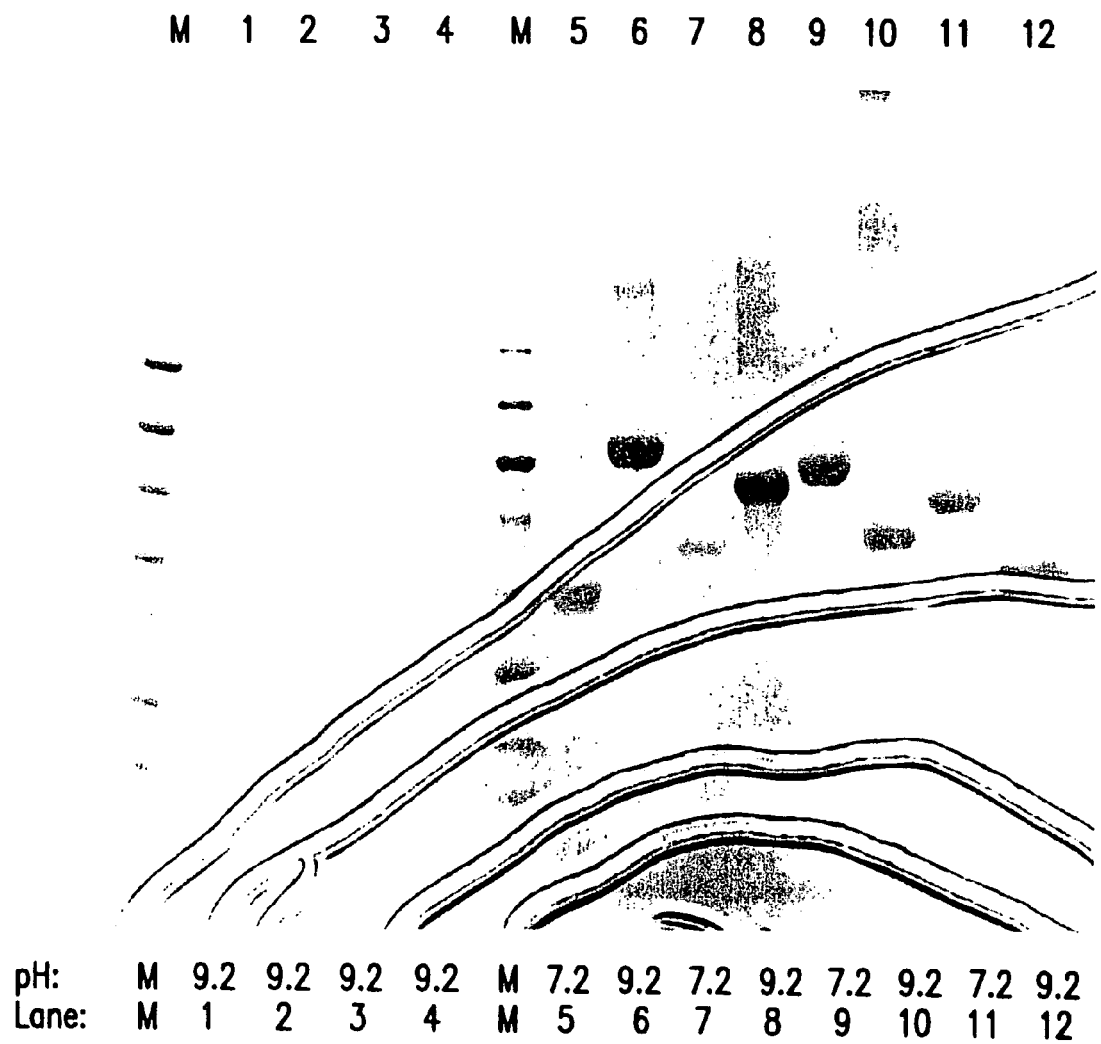

FIG. 12 is a photograph of a 4-20% SDS-PAGE gradient gel of 30 kD (lanes 1, 5, 12), 40 kD (lanes 2, 7, 10), 50 kD (lanes 3, 8, 11), and 60 kD (lanes 4, 6, 9) molecular weight markers prestained with Procion Red (lanes 1-4) or with eosin isothiocyanate (lanes 5-12) at the indicated pHs. M: molecular weight standard ladders (two different preparations).

Figure 13:
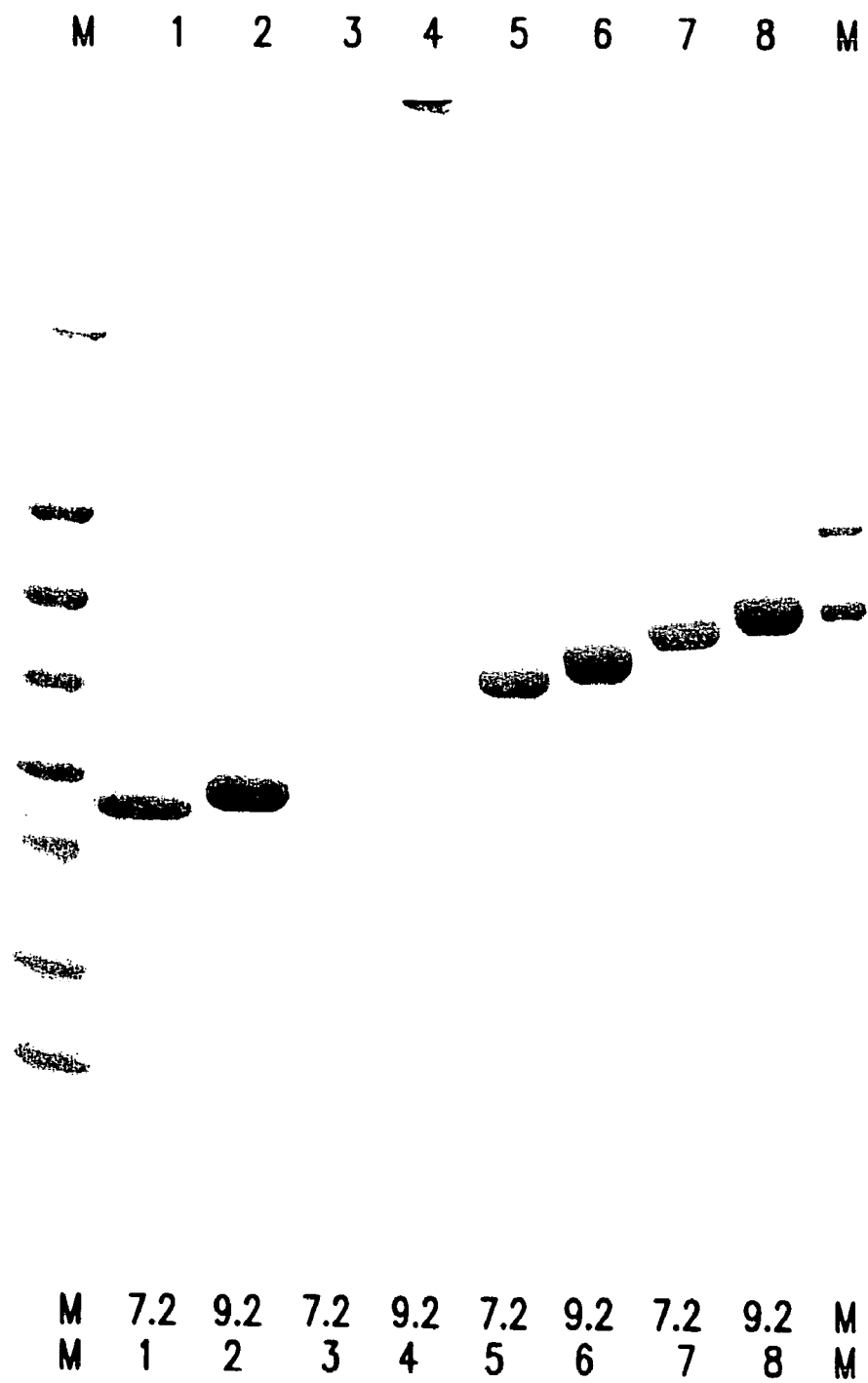

FIG. 13 is a photograph of a 4-20% SDS-PAGE gradient gel of 30 kD (lanes 1-2), 40 kD (lanes 3-4), 50 kD (lanes 5-6) and 60 kD (lanes 7-8) molecular weight markers prestained with malachite green isothiocyanate at the indicated pHs. M: molecular weight standard ladders (two different preparations).

DETAILED DESCRIPTION OF THE INVENTION

Definitions

In the description that follows, a number of terms conventionally used in the fields of molecular biology and protein engineering are utilized extensively. In order to provide a clear and consistent understanding of the specification and claims, and the scope to be given such terms, the following definitions are provided.

The term "polypeptide" is used herein to mean a sequence of contiguous amino acids, of any length. As used herein, the terms "peptide" or "protein" may be used interchangeably with the term "polypeptide."

The term "nucleic acid molecule" as used herein refers to a sequence of contiguous nucleotides which may encode a full-length polypeptide or a fragment of any length thereof, or may be non-coding.

The term "inclusion partner protein" is used herein to mean any protein or fragment, portion, derivative or variant thereof, which forms inclusion bodies upon expression in a host cell; nucleic acid molecules encoding inclusion partner proteins may be fused to those encoding polypeptides of interest in order to cause the polypeptide of interest to be co-expressed in the form of inclusion bodies in a host cell.

The term "gene fusion construct" as used herein means a nucleic acid molecule which is the product of the operative linkage or fusion of a nucleic acid molecule encoding a polypeptide of interest to a nucleic acid molecule encoding an inclusion partner protein. A gene fusion construct as defined herein may include additional nucleic acid sequences comprising expression signals (such as promoters or enhancers) which are recognized by a host cell and which direct the expression of the gene fusion construct to produce the polypeptide of interest.

The phrases "substantially all of the polypeptides are complexed with a dye" or "substantially all of the polypeptides are stained with a dye" or "substantially all of the polypeptides are labeled with a dye" may be used interchangeably and as used herein mean that substantially all of the polypeptides or proteins in a sample have been completely or substantially completely complexed, stained, or labeled with one or more dyes. Such completion of staining can be determined by any number of analytical techniques, although analysis of mobility and staining intensity by gel electrophoresis is preferred (see Examples below). For example, incomplete or partial staining of a protein sample results in a heterogeneous population of proteins, each of which may have a different mobility during gel electrophoresis. Upon complete or substantially complete staining, however, mobility will remain substantially unchanged even upon further staining (i.e., further incubation with dye). Thus, complete or substantially complete staining may be measured by such mobility changes, or the lack or substantial lack thereof. Alternatively or in addition to such mobility changes, completion of staining may be determined by changes in intensity of staining. Thus, upon complete or substantially complete staining in accordance with the invention, the stain intensity of a protein sample of interest, determined, for example, by gel electrophoresis, will not substantially change upon further staining (i.e., further incubation with dye).

Overview

The present invention provides a method for producing and isolating recombinant polypeptides from host cells, wherein the recombinant polypeptides are produced as inclusion bodies in the host cells. Specifically, the method involves (a) obtaining a host cell comprising a first nucleic acid molecule encoding a recombinant polypeptide operatively linked to a second nucleic acid molecule encoding an inclusion partner protein, thereby forming a gene fusion construct; and (b) cultivating the above host cell under conditions favoring production of the polypeptide as inclusion bodies in the host cell. The invention also provides the above method further comprising (c) isolating the inclusion bodies from the host cell, most preferably by centrifugation; and (d) releasing the polypeptide from the inclusion bodies. According to the present invention, the first nucleic acid molecule encoding the polypeptide may be obtained from a prokaryotic cell, particularly a bacterial cell and most particularly an *Escherichia coli* cell, or from a eukaryotic cell, particularly an animal cell, a plant cell or a yeast cell, more particularly a mammalian animal cell, and most particularly a human cell, and the second nucleic acid molecule encoding the inclusion partner protein may be obtained from any cell, preferably a bacterial cell, and most preferably an *Escherichia coli* cell. The inclusion partner protein used in the present invention may be any protein that forms an inclusion body upon expression in a host cell, and is preferably a bacterial protein, more preferably a bacterial thioredoxin or modified bacterial thioredoxin, and most preferably a carboxy terminal-truncated form of *E. coli* thioredoxin as described in more detail below. Preferably, the gene fusion construct is inserted into a vector prior to being introduced into the host cell. According to one aspect of the invention, the polypeptide of interest may be released from inclusion bodies, formed by the gene fusion construct, by cleavage with a chemical such as cyanogen bromide, or more preferably with an enzyme such as thrombin or enterokinase. According to another aspect, a nucleic acid sequence encoding a protein-specific cleavage site may be placed between the nucleic acid sequence encoding the inclusion partner protein and the recombinant polypeptide in the gene fusion construct; upon expression of the fusion protein as inclusion bodies in the host cells, the recombinant polypeptide may then be released therefrom by treating the inclusion bodies with an enzyme or other chemical that specifically recognizes and cleaves at the protein-specific cleavage site. The invention also provides the above-described methods wherein the gene fusion construct comprises plasmid pTrcprl-monomer, and provides plasmid pTrcprl-monomer. The invention is also directed to the above-described methods wherein the host cell is a bacterial cell, most preferably an *Escherichia coli* cell, and wherein the vector used is an expression vector, most preferably plasmids pTrc99A or pTrxfus. The invention also provides these vectors, and host cells, particularly bacterial cells and most particularly *Escherichia coli* cells, comprising these vectors. The invention further provides recombinant polypeptides made by the above methods, plasmid pTrcprl-monomer, and plasmid pTrxA-concat.

In another preferred embodiment, the invention provides methods for making a protein molecular weight ladder, which is preferably prestained, and a protein molecular weight ladder produced by these methods.

Although the present invention is most particularly directed to methods for the production of a fragment of the gene 32 protein of bacteriophage T4, KpnI methylase, or Dead-Box protein, it will be readily appreciated by one of ordinary skill in the art that using the methods of the present invention, any polypeptide comprising a sequence of contiguous amino acids of any length may be produced as inclusion bodies in a host cell and isolated therefrom.

Gene Fusion

The methods of the present invention utilize the technique of gene fusion to produce a gene fusion construct comprising the nucleic acid molecule encoding a first polypeptide operatively linked to a second nucleic acid molecule encoding an inclusion partner protein. The nucleic acid molecule encoding the first polypeptide may be obtained from a bacterial cell, particularly an *E. coli* cells; from an animal cell, preferably a mammalian cell and most preferably a human cell; a plant cell; or a yeast cell. As described in more detail below, the nucleic acid molecule encoding the inclusion partner protein may be obtained from any cell, preferably from a bacterial cell, and most preferably from an *Escherichia coli* cell. Methods for construction of gene fusion constructs comprising a DNA sequence encoding a desired polypeptide, fused to a prokaryotic DNA sequence, are well-known in the art (see, e.g., Sambrook, J., et al., *Molecular Cloning: A Laboratory Manual, 2nd Ed.*, Cold Spring Harbor, N.Y.: Cold Spring Harbor Laboratory Press, pp. 17.2-17.9 (1989); Ausubel, F. M., et al., eds., *Current Protocols in Molecular Biology*, New York: John Wiley & Sons, Inc., pp. 16.4.1-16.8.14 (1994)). Other suitable methods that are routine to one of ordinary skill in the art may also be used equivalently in the methods of the present invention.

Vectors and Host Cells

The present invention also relates to vectors which comprise the isolated DNA molecules of the present invention, host cells which are genetically engineered with the recombinant vectors, and methods for the production of a recombinant polypeptide using these vectors and host cells.

The vector used in the present invention may be, for example, a phage or a plasmid, and is preferably a plasmid. Preferred are vectors comprising cis-acting control regions to the nucleic acid encoding the polypeptide of interest. Appropriate trans-acting factors may be supplied by the host, supplied by a complementing vector or supplied by the vector itself upon introduction into the host.

In certain preferred embodiments in this regard, the vectors provide for specific expression, which may be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids or bacteriophages, and vectors derived from combinations thereof, such as cosmids and phagemids.

The DNA insert should be operatively linked to an appropriate promoter, such as the phage lambda PL promoter, the *E. coli* lac, trp and tac promoters. Other suitable promoters will be known to the skilled artisan. The gene fusion constructs will further contain sites for transcription initiation, termination and, in the transcribed region, a ribosome binding site for translation. The coding portion of the mature transcripts expressed by the constructs will preferably include a translation initiation codon at the beginning, and a termination codon (UAA, UGA or UAG) appropriately positioned at the end, of the polynucleotide to be translated.

The expression vectors will preferably include at least one selectable marker. Such markers include tetracycline or ampicillin resistance genes for culturing in *E. coli* and other bacteria.

Among vectors preferred for use in the present invention include pQE70, pQE60 and pQE-9, available from Qiagen; pBS vectors, Phagescript vectors, Bluescript vectors, pNH8A, pNH16a, pNH18A, pNH46A, available from Stratagene; pcDNA3 available from Invitrogen; and pGEX, pTrxfus, pTrc99a, pET-5, pET-9, pKK223-3, pKK233-3, pDR540, pRIT5 available from Pharmacia. Other suitable vectors will be readily apparent to the skilled artisan.

Representative examples of appropriate host cells include, but are not limited to, bacterial cells such as *E. coli*, *Streptomyces* spp., *Erwinia* spp., *Klebsiella* spp. and *Salmonella typhimurium*. Preferred as a host cell is *E. coli*, and particularly preferred are *E. coli* strains DH10B and Stbl2, which are available commercially (Life Technologies, Inc; Rockville, Md.).

Inclusion Partners

It has been unexpectedly discovered in the present invention that use of a modified version of the gene encoding the inclusion partner protein will induce the host cell to produce the fusion protein, comprising the polypeptide of interest, as intracellular inclusion bodies. As used herein, the term "modified version of a gene" means a version of a gene comprising an alteration of the normal or most commonly encountered sequence of the gene, which results in the expression of the encoded protein, in a fused or unfused state, in inclusion bodies in a host cell. Such alterations may include, but are not limited to, deletions, substitutions, insertions, point mutations, and the like.

Preferred inclusion partner proteins for use in the present invention include, but are not limited to, modified versions of *E. coli* maltose-binding protein (Betton and Hofnug, *J. Biol. Chem.* 271:8046-8052 (1996)), *E. coli* RNAse II (Coburn and Mackie, *J. Biol. Chem.* 271:1048-1053 (1996)), *E. coli* alkaline phosphatase (Derman and Beckwith, *J. Bacteriol.* 177:3764-3770 (1995); Georgiou et al., *Appl. Env. Microbiol.* 52:1157-1161 (1986)), *E. coli* phospholipase A (Dekker et al., *Eur. J. Biochem.* 232:214-219 (1995)), *E. coli* 3-lactamase (Rinas and Bailey, *Appl. Env. Microbiol.* 59:561-566 (1993); Georgiou et al., *Appl. Env. Microbiol.* 52:1157-1161 (1986)), *Salmonella typhimurium* MalK protein (Schneider et al., *Prot. Exp. Purif.* 6:10-14 (1995)), *Clostridium thermocellum* endoglucanase D (Tokatlidis et al., *FEBS Lett.* 282:205-208 (1991)), *Bacillus thuringiensis* subsp. *aizawai* IPL7 insecticidal proteins (Oeda et al., *J. Bacteriol.* 171:3568-3571 (1989), human procathepsin B (Kuhelj et al., *Eur. J. Biochem.* 229:533-539 (1995)), porcine interferon-γ (Vandenbroeck et al., *Eur. J. Biochem.* 215:481-486 (1993)), T5 DNA polymerase (Chatterjee et al., *Gene* 97:13-19 (1991)), and *E. coli* thioredoxin (Hoog et al., *BioSci. Rep.* 4:917-923 (1984)). More preferable for use in the present invention is a modified *E. coli* thioredoxin, which as used herein is a thioredoxin protein having the ability to form inclusion bodies (in fused or unfused constructs) upon expression in a host cell. Particularly preferred is a deletion mutant of the *E. coli* thioredoxin encoded by the trxA gene, and most particularly the carboxy terminal-truncated form of *E. coli* trxA having a nucleotide sequence as set forth in SEQ ID NO:8, hereinafter designated pTrxA-concat. The recombinant host cell comprising pTrxA-concat, *E. coli* DH10B (pTrxA-concat), was deposited on Jan. 6, 1997, with the Collection, Agricultural Research Culture Collection (NRRL), 1815 North University Street, Peoria, Ill. 61604 USA, as Deposit No. NRRL B-21653.

Truncated versions of trxA that may be used in the present invention include those wherein 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids are deleted from the carboxy terminus of thioredoxin, preferably those wherein 23, 24, 25, 26, 27, 28, 29, 30, 31, 32 or 33 amino acids are deleted, and most preferably those wherein 23 amino acids are deleted (pTrxfusprl10A).

Methods for making and expressing modified gene fusion constructs, such as a construct encoding a modified or truncated thioredoxin, are well-known to one of ordinary skill in the art and are amply described in the literature (see, e.g., Winnacker, *From Genes to Clones*, New York: VCH Publishers, pp. 451-481 (1987)), and in detail in the Examples below. To determine if a particular modified gene fusion construct induces the production of inclusion bodies in a host cell, the construct may be transferred into a host cell and expressed as described below. A suspension of host cells may then be examined for the presence of inclusion bodies by any means, such as microscopy (e.g., phase contrast, Nomarski interference, electron or fluorescence microscopy), suitable for the detection of the presence of inclusion bodies within individual host cells.

For use in the present invention, the inclusion partner nucleic acid sequence may be inserted into the chromosome of the host cell, or in a vector which is preferably an expression vector. Particularly preferred as expression vectors in the present invention are well-known expression vectors such as pAR (for lacZ), pATH (for trpE), pMAL (for malE), pGEX (for GST), or pTrxfus (for trxA). These vectors and others that may also be suitable are available commercially, for example from Pharmacia (Piscataway, N.J.). Alternatively, other well-characterized vectors known in the art may be used to carry out the methods of the present invention.

As described above, the methods of the present invention are suitable for production of any polypeptide of any length, and are particularly suitable for producing short polypeptides, or those that are toxic to the host cells, which otherwise would not be expressed by the host cells in significant quantities. Methods for isolation of nucleic acid sequences encoding a polypeptide of interest from a variety of sources are well-known in the art (see, e.g., Sambrook, J., et al., *Molecular Cloning: A Laboratory Manual*, 2nd Ed., Cold Spring Harbor, N.Y.: Cold Spring Harbor Laboratory Press, (1989)). Once the nucleic acid sequence encoding the polypeptide of interest has been isolated, it is operatively linked or fused to the modified inclusion partner nucleic acid from above, forming a vector, preferably an expression vector, comprising the gene fusion construct to be used in transforming the host cells. Particularly preferred as a gene fusion construct is plasmid ptcprl-monomer. Methods for fusion of the nucleic acid sequence encoding a polypeptide of interest to a truncated inclusion partner nucleic acid sequence, and insertion into an expression vector are routine to one of ordinary skill in the art (see, e.g., Ausubel, F. M., et al., eds., *Current Protocols in Molecular Biology*, New York: John Wiley & Sons, Inc., pp. 16.4.1-16.8.14 (1994)).

Expression of Recombinant Protein as Inclusion Bodies

For use in the present invention, the gene fusion construct may be inserted into the chromosome of the host cell, or in a vector which is preferably an expression vector. Introduction of the gene fusion construct into the host cell to produce a transformed host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986). Once transformed host cells have been obtained, the cells may be cultivated under any physiologically compatible conditions of pH and temperature, in any suitable nutrient medium containing assimilable sources of carbon, nitrogen and essential minerals that support host cell growth. Recombinant protein-producing cultivation conditions will vary according to the type of vector used to transform the host cells. For example, certain expression vectors comprise regulatory regions which require cell growth at certain temperatures, or addition of certain chemicals or inducing agents to the cell growth medium, to initiate the gene expression resulting in the production of the recombinant polypeptide. Thus, the term "recombinant polypeptide-producing conditions," as used herein, is not meant to be limited to any one set of cultivation conditions. Appropriate culture media and conditions for the above-described host cells and vectors are well-known in the art.

It has been unexpectedly found in the present invention that cultivating the host cells transformed with the gene fusion constructs provided herein will result in the production of the recombinant polypeptide of interest as inclusion bodies. Thus, routine recombinant polypeptide-producing conditions may therefore be considered to favor production of the recombinant polypeptide as inclusion bodies in the host cell, and may be used to produce recombinant polypeptides as inclusion bodies according to the present invention; the use of unusual culture conditions or undue experimentation are not required.

Isolation and Purification of Recombinant Polypeptide

As is well-known to one of ordinary skill in the art, methods for the production of polypeptides by recombinant DNA techniques typically are designed to minimize the production of the polypeptides in inclusion bodies in the host cells, due to perceived and real difficulties in isolating the polypeptides from the inclusion bodies. According to the present invention, however, the production of a recombinant polypeptide in inclusion bodies may be used advantageously to provide for the rapid isolation and purification of the polypeptide.

Following its production as inclusion bodies in the host cells, the gene fusion product comprising the polypeptide of interest may be isolated by several techniques. To liberate the inclusion bodies from the host cells, the cells must be lysed or ruptured. This lysis may be accomplished by contacting the cells with a hypotonic solution, by treatment with a cell wall-disrupting enzyme such as lysozyme, by sonication, by treatment with high pressure, or by a combination of the above methods. Other methods of bacterial cell disruption and lysis that are known to one of ordinary skill may also be used. Preferably, bacterial cells are ruptured by treatment with lysozyme followed by sonication; such treatment will yield a mixture of cellular debris comprising the inclusion bodies, which are not disrupted by this treatment.

Following disruption, the inclusion bodies are separated from the cellular debris by any technique suitable for separation of particles in complex mixtures. Preferred such techniques include centrifugation, or the use of an automated particle separator such as those commercially available from, for example, Coulter Electronics (Hialeah, Fla.). Most preferred for isolating inclusion bodies is centrifugation. By the present invention, inclusion bodies may be isolated by centrifuging the cellular debris mixture from above at about 1-25,000×g, preferably at about 100-20,000×g, more preferably at about 5,000-15,000×g, and most preferably at about 10,000×g. Preferably, centrifugation is conducted at about 4E-10EC for about 15-60 minutes, most preferably at about 4EC for about 30 minutes. Following centrifugation, the cellular debris contained in the supernatant is removed from the pelleted inclusion bodies and the pellet used for purification of the recombinant polypeptide of interest.

In preparation for purification, the gene fusion product contained in the inclusion bodies, comprising the recombinant polypeptide, is solubilized. Solubilization is preferably accomplished by treatment with a denaturing agent, preferably guanidinium hydrochloride or urea, and most preferably about 8M urea.

Prior to, during or following solubilization of the inclusion bodies, the recombinant polypeptide of interest may optionally be cleaved from the inclusion partner protein by techniques that are well-described in the art (see, e.g., Ausubel, F. M., et al., eds., *Current Protocols in Molecular Biology*, New York: John Wiley & Sons, Inc., pp. 16.4.5-16.4.17 (1994)). It will be understood by one of ordinary skill, however, that production of recombinant polypeptides by the present invention does not necessarily require such cleavage. This cleavage may be accomplished by a chemical cleavage method, for example by contacting the inclusion bodies with a polypeptide-releasing amount of a chemical cleavage agent under conditions favoring the release of the polypeptide from the inclusion bodies. Preferred chemical cleavage agents include cyanogen bromide, hydroxylamine, or low pH solutions (acid hydrolysis). Alternatively, and more preferably, cleavage of the inclusion partner protein is accomplished by an enzymatic cleavage method, preferably by contacting the inclusion bodies with a polypeptide-releasing amount of an enzymatic cleavage agent under conditions favoring the release of the polypeptide from the inclusion bodies. Preferred enzymatic cleavage agents include factor Xa (for gene fusion products comprising a malE or GST inclusion partner) or thrombin (for gene fusion products comprising a GST inclusion partner), and particularly preferred is enterokinase (for gene fusion products comprising a trxA inclusion partner). These chemical and enzymatic cleavage methods are preferably carried out under conditions favoring the release of the polypeptide from the inclusion bodies, which are well-known to one of ordinary skill in the art (see, e.g., Ausubel, F. M., et al., eds., *Current Protocols in Molecular Biology*, New York: John Wiley & Sons, Inc., pp. 16.4.5-16.4.17 (1994)). Such release may result in solubilization of the peptide of interest and thus further solubilization may be unnecessary. Alternatively, cleavage of the inclusion partner protein from the polypeptide may be facilitated during the formation of the gene fusion construct. In such a scheme, a nucleic acid sequence encoding a protein-specific cleavage site may be placed between the nucleic acid sequence encoding the inclusion partner protein (such as the modified thioredoxin) and the recombinant polypeptide in the gene fusion construct; upon expression of the fusion protein as inclusion bodies in the host cells, the recombinant polypeptide may then be isolated by treating the inclusion bodies with an enzyme (such as thrombin or enterokinase) or a chemical (such as cyanogen bromide) that specifically recognizes and cleaves at the protein-specific cleavage site. Cleavage of the inclusion partner protein may alternatively be performed during or following any of the subsequent steps described below.

After solubilization, the gene fusion product or the cleaved recombinant polypeptide may be refolded by dialysis to remove the denaturing agent. Dialysis is preferably performed for about 18-48 hours at about 4EC against an isotonic buffered salt solution.

Following solubilization and optional refolding, the gene fusion product or cleaved recombinant polypeptide may be purified by any of a variety of protein purification techniques that are well-known to one of ordinary skill in the art. Suitable techniques for purification include, but are not limited to, ammonium sulfate or ethanol precipitation, acid extraction, electrophoresis, immunoadsorption, anion or cation exchange chromatography, phosphocellulose chromatography, hydrophobic interaction chromatography, affinity chromatography, immunoaffinity chromatography, size exclusion chromatography, liquid chromatography (LC), high performance LC (HPLC), fast performance LC (FPLC), hydroxylapatite chromatography and lectin chromatography. Most preferably LC, HPLC or FPLC is employed for purification.

As described above, any recombinant polypeptide may be produced and isolated from host cells by the methods of the present invention. In particular, it is possible to produce recombinant thioredoxin by these methods. In such a scheme, thioredoxin, or a fragment thereof, may be produced by a series of steps comprising (a) modifying the thioredoxin gene, (b) transferring the modified thioredoxin gene to a host cell, and (c) culturing the host cell under conditions favoring production of thioredoxin as inclusion bodies in the host cell. These modification, transfer and culture steps may be carried out for thioredoxin as described above for production of any polypeptide, and as described in more detail in the Examples below.

Production of Protein Molecular Weight Ladders

In another aspect, the methods of the present invention may be used to prepare a protein molecular weight ladder to be used as a molecular weight or molecular sizing standard in protein analysis techniques such as electrophoresis. In this embodiment, described in greater detail below in Examples 3-9, a series of fusion proteins may be made, wherein the inclusion partner protein is linked to one or more recombinant polypeptides or fragments thereof. For example, a nucleic acid molecule encoding a modified thioredoxin inclusion partner protein may be inserted into a vector, preferably an expression vector, to form a fusion vector such as plasmid pTrxA-concat (FIG. 4; SEQ ID NO:8). This vector may then be linked to single or multiple fragments of a recombinant polypeptide such as thioredoxin (FIG. 5; SEQ ID NO:11), *E. coli* Dead-Box protein (FIG. 6; SEQ ID NO:14), KpnI methylase (FIG. 7; SEQ ID NO:17) or 264-bp modified T4 gene 32 protein (FIG. 1; SEQ ID NO:1), each of a chosen size (e.g., 5 kD or 10 kD). After insertion of the nucleic acid molecule or vector into the host cell (i.e., transformation of the host cell), the polypeptides may then be produced by expression of the nucleic acid molecules in the host cells. It will be obvious to one of ordinary skill in the art that several expression scenarios are possible. For example, the methods of the present invention may be used to produce a nucleic acid molecule encoding a plurality of the polypeptides forming the molecular weight ladder, or to produce multiple nucleic acid molecules each of which encodes a different molecular weight polypeptide of the ladder. Host cells may then be transformed with a nucleic acid encoding a plurality of such polypeptides, or with multiple nucleic acid molecules each encoding a different molecular weight polypeptide. Alternatively, multiple host cells may be transformed, each with a single nucleic acid molecule encoding a different polypeptide of the molecular weight ladder; in this scenario, polypeptides produced by the host cells will be admixed to form the molecular weight ladder. In each of these scenarios, expression of these constructs will preferably produce inclusion bodies in the host cells comprising polypeptides from as small as 5-10 kD to as large as 250-330 kD. Furthermore, the molecular weight increments of the ladder produced by the present methods may be defined by simply altering the length or number of copies of the recombinant polypeptide gene linked to the inclusion partner protein gene fusion construct. Thus, it is possible according to the present invention to produce a protein ladder comprising a collection of proteins ranging, for example, from about 5 kD to about 300 kD, preferably from about 5 kD to about 250 kD, and more preferably from about 10 kD to about 220 kD, in increments of, for example, 5 kD, 10 kD, 20 kD, 25 kD, 50 kD, 100 kD or larger. Of course, it will be understood by one of ordinary skill that other molecular weight or sizing increments may be more suitable for certain applications, and may be prepared by only minor modifications of the present methods (such as by increasing or decreasing the length of the gene encoding the fused recombinant polypeptide as described above); such methods and compositions may thus be provided without departing from the scope of the present invention or any embodiment thereof.

In a preferred embodiment, the protein molecular weight ladders prepared as described above may be unstained, or may be prestained with one or more protein-binding dyes to facilitate the use of the ladders in techniques requiring prestained protein ladders such as Western blotting. According to the invention, any of a number of protein-binding dyes may be used to stain proteins or the molecular weight ladders of the invention, to produce the prestained ladders of the invention. Any dye that binds covalently to one or more of the ladder proteins may be used, including visible dyes (chromophores), fluorescent dyes (fluorophores), phosphorescent dyes (phosphors) and the like. Preferred dyes in this regard include, but are not limited to, remazol brilliant blue R (RBBR), eosin isothiocyanate, malachite green isothiocyanate, reactive orange (also known as procion yellow), procion red, fluorescein isothiocyanate, rhodamine isothiocyanate, eosin iodoacetamide, reactive black 5, Remasol brilliant violet 5R, reactive orange 14, and the like. Particularly preferred for use in the present methods are RBBR, eosin isothiocyanate and malachite green isothiocyanate. These and other dyes that may be used in the present methods are available commercially, for example from Sigma/Aldrich (St. Louis, Mo.) and Molecular Probes (Eugene, Oreg.).

According to the invention, prestained molecular weight ladders may be produced by incubating one or more of the ladder proteins, which may be naturally occurring or produced recombinantly as directed above, with one or more of the above-noted dyes in a buffered aqueous solution under conditions of controlled temperature, time, and solution pH. Preferably, the ladder proteins are suspended in a buffered aqueous solution (such as a Tris-, phosphate-, carbonate-, or HEPES-buffered saline solution comprising NaCl at about 10-300 mM, preferably at about 50-200 mM) at a concentration of about 0.1 to about 25, about 0.1 to 10, or about 0.5 to 10 $A_{280}$ units/ml, more preferably at a concentration of about 1-10, about 1-5, or about 1-4 $A_{280}$ units/ml. To the solution of protein(s), one or more of the above dyes may be added at concentration ranges that are specific for each dye, typically in the range of about 0.2 mg/ml to about 1000 mg/ml, about 0.2 mg/ml to about 500 mg/ml, about 0.2 mg/ml to about 100 mg/ml, about 5 mg/ml to about 200 mg/ml, about 10 mg/ml to about 200 mg/ml, or about 10 mg/ml to about 100 mg/ml. For example, RBBR may be added to the protein solution at a final concentration of about 0.3-50 mg/ml, preferably at about 5-40 mg/ml, and more preferably about 10-30 mg/ml. Eosin isothiocyanate may be added to the protein solution at a final concentration of about 1-30 mg/ml, and more preferably about 7-10 mg/ml. Malachite green isothiocyanate may be added to the protein solution at a final concentration of about 5-30 mg/ml, more preferably about 20-30 mg/ml. Optimal concentrations for other dyes that may be used to stain the proteins and molecular weight ladders according to the present methods may be determined by one of ordinary skill without undue experimentation, using the above-noted concentration ranges as guidelines.

The staining of the protein ladders should also be conducted under conditions of controlled solution pH and/or temperature. Preferably, the solution is buffered to a pH (measured at about room temperature (i.e., about 20EC-25EC) prior to addition of the proteins, ladders, and dye(s)) of about 7-12, about 7-11, about 8-11, or about 8.5-10.5, preferably about 7.2-9.7, more preferably about 8.2-9.7, and most preferably about 9.2-9.7. During the staining reaction, the solutions should be incubated at a temperature of about 4° C. to about 90° C., about 4° C. to about 80° C., preferably at about room temperature (i.e., about 20° C.-25° C.) to about 80° C., about 35° C. to about 80° C., about 40° C. to about 75° C., about 45° C. to about 70° C., about 45° C. to about 70° C., about 50° C. to about 70° C., about 45° C. to about 65° C., more preferably at a temperature of about 50° C. to about 60° C., and most preferably at a temperature of about 50° C. For production of stained proteins or ladders, the protein-dye solutions should be incubated under the above-noted conditions for about 4-48 hours, prefrably about 6-48 hours, more preferably about 4-24 hours, about 6-24 hours, about 8-24 hours, about 10-24 hours, about 12-24 hours, and most preferably about 12-18 hours (i.e., "overnight," as that term will be understood by the skilled artisan). Following incubation, the stained protein(s) or molecular weight ladders may be isolated from unconjugated dye and any other impurities by a variety of art-known methods (e.g., dialysis, chromatography, gel diffusion, etc.), and may be stored in solution at −70° C. to 4° C., or they may be lyophilized and stored at −70° C. to room temperature (i.e., about 20° C.-25° C.) until use.

In a particularly preferred such embodiment, the prestained protein ladder may comprise a collection of protein molecular weight markers that are evenly spaced on SDS-PAGE and that further comprise a reference protein band stained with a different color from the other bands, to allow easy orientation of all of the bands on the gel. For example, such a prestained ladder preparation may comprise a collection of bands wherein one band (a reference band) is stained with eosin isothiocyanate and the remaining bands are stained with RBBR. Such an approach is described in full detail in Example 4 below.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Materials and Methods

The following materials and methods were generally used in the examples, unless otherwise specified in a particular example.

Materials

All enzymes including restriction enzymes, T4 DNA ligase, Taq DNA polymerase and thermosensitive alkaline phosphatase were obtained from Life Technologies, Inc. (LTI; Rockville, Md.) unless otherwise stated. The *E. coli* expression vector pTrc99A was obtained from Pharmacia (Piscataway, N.J.); pTrxfus was from Genetics Institute (Cambridge, Mass.) or Invitrogen (San Diego, Calif.), pRE1 was obtained from Dr. McKenney (Reddy et al., *Nucl. Acids Res.* 17:10473-10488 (1989)). Toyo-Pearl AF chelate-650M resin was purchased from TosoHaas (Montgomeryville, Pa.). The *E. coli* expression host DH10B with or without pRK248c1 (tetracycline$^r$) and Stbl2 were from Life Technologies, Inc. (Rockville, Md.).

Remasol brilliant blue R (RBBR) and malachite green were obtained from Aldrich and eosin isothiocyanate was obtained from Molecular Probes. Bovine aprotinin was obtained from Bayer. The cloned proteins were purified, as fully described below, from *E. coli* strains which contained plasmids coding for eight proteins ranging in size from 10 kDa to 160 kDa. The buffer components were all reagent grade or higher. The diafiltration unit was a Filtron Mini Ultrasette equipped with an Omega 3000 molecular weight cutoff membrane. G-25 medium resin was obtained from Pharmacia. Other reagents and components were obtained from commercial laboratory supply sources that will be familiar to the skilled artisan.

Recombinant DNA Construction

A 264 bp (SEQ ID NO:1) AvaI fragment was derived from pPrL2107 (U.S. Pat. No. 5,449,758). This fragment is a part of T4 gene 32 protein which has been highly modified. This AvaI fragment was used to make multimers (see U.S. Pat. No. 5,449,758) in pPrL2001. A clone with 12 inserts was selected and was designated as pPrl 2738. The cloned fragment was recloned in pTrc99A as follows: the recombinant plasmid was digested with EcoRI and blunt ended with Klenow fragment in the presence of dNTPs; digested with NcoI and the fragment was purified by GENE CLEAN™ (Bio101). The vector, pTrc99A, was digested with SalI, blunt ended with Klenow fragment, and digested with NcoI. The gel purified vector was ligated with the gel purified fragment and transformed into DH10B. The clone was designated as pTrcprl.

To make a monomer, pTrcprl was completely digested with AvaI to remove multimers and the vector was self-ligated. This construct contains a 261 bp (SEQ ID NO:2) fragment with a single AvaI site and was expected to produce a 10 kD protein. The plasmid was designated as pTrcprl-monomer.

To generate clones to produce individual proteins from 20 kD to 220 kD, the 264 bp AvaI fragment from pPrL2107 was used to make multimers in pTrcprl-monomer at the AvaI site. Since the 264 bp fragment (SEQ ID NO:1) contains an internal methionine residue, it was altered to a lysine residue by site-directed mutagenesis in order to stop any internal initiation. The ligation was carried out at room temperature (22° C.) by using 100:1 pmol ratio of insert and vector. Individual clones with correct inserts (two, three, four, etc.) were selected by the size of the insert after digestion with NcoI and HindIII. The plasmids were designated as pTrcprl20, pTrcprl30, pTrcprl40, and so on, to produce 20 kD, 30 kD, 40 kD, etc. proteins respectively.

A clone was also generated which contained a part of *E. coli* thioredoxin (truncated) under control of the lambda pL promoter to produce a 10 kD protein. This construct contained 86 out of 108 amino acids of thioredoxin plus six histidine residues at the carboxy end, which provided a His tag to facilitate purification of the expressed protein. In alternative approaches, a maximum of 33 amino acids were deleted from the thioredoxin protein, producing a construct comprising 75 out of 108 amino acids of thioredoxin plus the His tag. The oligonucleotides used to clone the fragment were T CTA AGG AAA TAC TTA <u>CATATG</u> AGC G (SEQ ID NO:3) and TA TTA <u>CTGCAG</u> TTA GTG GTG GTG GTG GTG GTG TTC ACC GTT TTT GAA CAG CAG CAG (SEQ ID NO:4). The oligonucleotides were used for PCR using pTrxfus as a template. The PCR product was digested with NdeI and PstI (incorporated in the oligonucleotides underlined) and cloned into pTrxfus digested with NdeI and PstI. The plasmid was designated as pTrxfusprl10A (SEQ ID NO:5).

The oligonucleotides TAA TAA <u>CCATGG</u> CAT ATG AGC GAT AAA ATT ATT CAC (SEQ ID NO:6) and ATT ATA <u>CCCGAG</u> TCC ACC ACG GAT GCC ATA TTT CGG (SEQ ID NO:7) with NcoI (bold, underlined and italics), NdeI (bold italics) and AvaI (bold underlined) were used to generate an alternative vector for making multimers as follows: The oligonucleotides were used to generate a PCR product using pTrxfus as a template. The PCR product was digested with NcoI and AvaI and cloned into pTrcprl-monomer to replace the NcoI-AvaI fragment of modified T4 gene 32 gene. This plasmid was designated as pTrxA-concat (SEQ ID NO:8). This construct contained amino acids 1-75 from thioredoxin, glycine as the 76th amino acid, and amino acids 77-90 from pTrcprl-monomer including the 6 carboxy-terminal histidine residues. This construct was made to generate fusion proteins by in-frame ligation of an AvaI fragment or multimers of AvaI fragment as discussed above. To make multimers, we have used AvaI fragments generated by PCR from several test genes such as thioredoxin, DEAD-box or KpnI methylase. The oligonucleotides used to generate an AvaI fragment from the thioredoxin gene (Hoog et al., *Bioscience Reports* 4:917-923 (1984)) were: TAA TAA CTC GGG AGC GAT AAA ATT ATT CAC CTG (SEQ ID NO:9) and ATA ATA CCC GAG TTT GGT TGC CGC CAC TTC ACC (SEQ ID NO:10). The PCR product (SEQ ID NO:11) was digested with AvaI and ligated to AvaI digested and dephosphorylated pTrxA-concat using 100 pmol of insert and 1 pmol of vector. Clones with single or multiple inserts were selected by estimating the size of the insert after digestion with NcoI and PstI. Finally, the desired inserts were cloned as NdeI-PstI fragment into pTrxfus. Thus, these clones will produce thioredoxin-(thioredoxin)$_n$ fusion proteins as 20 kD, 30 kD, 40 kD, etc. The oligonucleotides used to generate an AvaI fragment from DEAD-box gene (Toone et al., *J. Bacteriol.* 173(11):3291-3302 (1991)) were TAA TAA CTC GGG AAG CTG ACT AAT CCG GAA GTA G (SEQ ID NO:12) and ATT ATT CCC GAG CAG TGC GCG GTA TTG ATC CAG (SEQ ID NO:13). The PCR product (SEQ ID NO:14) was generated using *E. coli* chromosome as template. The PCR product digested with AvaI and ligated with pTrxA-concat as above. Clones with various inserts were selected and recloned in pTrxfus as above. These clones were designed to produce thioredoxin-(DEAD-box)$_n$ fusion proteins as 15 kD, 20 kD, 25 kD, etc. To make thioredoxin-KpnI methylase fusions proteins, the oligonucleotides used were GA TTA CTC GGG GCA CAT AAA ATG CTA AAA GAT ACA (SEQ ID NO:15) and TC TAA CCC GAG TAA GAT CGT TTT TCT TGA ACC ACC (SEQ ID NO:16). The template used for PCR was a KpnI methylase clone (Chatterjee et al., *Nucleic Acids Res.* 19:6505-6509 (1991)). The PCR product (SEQ ID NO:17) was digested with AvaI and ligated to pTrxA-concat and finally, an NdeI-PstI fragment was subcloned into pTrxfus plasmid. This plasmid was generated to produce a 40 kD thioredoxin-KpnI methylase fusion protein.

Expression of Proteins

*E. coli* DH10B or Stbl2 (LTI; Rockville, Md.) containing pTrcprl constructs were grown at 37° C. in buffer-rich media containing ampicillin at 100 µg/ml. Clones were grown to an $OD_{590}$=1.0 and induced for 3 hours with IPTG to a final concentration of 1 mM. Clones were incubated at 37EC for 3 hours. pTrxfus constructs were grown at 30° C. in buffer-rich media containing ampicillin at 100 µg/ml and tetracycline at 15 µg/ml. Clones were grown to an $OD_{590}$=1.0 and induced by heating to 42° C. for 30 minutes followed a 3 hour outgrowth at 37° C. Cells were resuspended in 1 ml of sonication buffer (10 mM Tris-HCl 7.5, 1 mM EDTA, and 10 mM β-mercaptoethanol) followed by sonicating for 3×10 seconds. Removed 100 µl for whole cell extract. An aliquot was removed to analyze proteins as total protein. The sonicated sample was spun for 10 minutes at 4EC and transferred supernatant to an eppendorf tube (soluble).

Samples (total and soluble fractions) were applied to a 4-20% tris-glycine gel to examine protein.

Purification of Proteins

The cells were slurried in a 1 g:2 mL ratio of 20 mM Tris-HCl, 2 mM $MgCl_2$, pH 8.0 buffer. Benzonase, a recombinant endonuclease from American International Chemical, was added at a ratio of 25 units per mL of slurry. The cells were cracked with two passes through a high pressure laboratory homogenizer, Model MINI-LAB, type 7.30VH mm from APV Rannie, at 12,000 psi. The sample was then spun at 10,000×g for 30 minutes in an RC-5 centrifuge to pellet the inclusion bodies while leaving most of the cell debris in the supernatant liquid. The inclusion body pellet was then washed twice at about 20-25° C. with sterile water using an Ultra Torrax Tissuemizer from Tekmar to fully suspend the pellet. The pellet was then made soluble in 8M Urea, 100 mM $H_2NaPO_4$, 4 mM imidazole, pH 8.4 buffer and loaded on to a Toyopearl AF Chelate-650M resin from TosoHaas. Before loading the sample, the resin was charged with 3 column volumes of a IM nickel sulfate solution, washed with three column volumes of water and then equilibrated with three column volumes of 8M urea, 100 mM $H_2NaPO_4$, 4 mM imidazole, pH 8.4 (buffer). After loading the sample, the column was washed with 10 column volumes of buffer, and the protein was then eluted in a single fraction with 8M urea, 100 mM $H_2NaPO_4$, pH 3.5, and precipitated via dialysis against water containing 5 mM EDTA; EDTA was included to chelate free nickel ions which degraded the proteins upon long-term storage. The precipitate was spun down at 10,000×g in an RC-5 centrifuge and then solubilized in 1% SDS/water.

Remasol Brilliant Blue R Labeling

The 10, 15, 20, 25, 30, 40, 70, 100, and 160 kDa proteins were diluted in 1% SDS $H_2O$ to 8 $A_{280}$ units/ml. Each protein solution was combined with an equal volume of the buffer 280 mM sodium phosphate, 160 mM sodium chloride, 1% (w/v) SDS, pH 9.2, and warmed to 50EC for 15 minutes. Stock solutions of RBBR (20 mg/ml and 60 mg/ml) were prepared in 140 mM sodium phosphate, 80 mM sodium chloride, 1% (w/v) SDS, pH 9.2, vortexed, and incubated for 15 minutes at 50° C. The 10, 15, 20, 30, 70, and 160 kDa protein solutions were then individually mixed with an equal volume of the warmed 60 mg/ml RBBR stock, vortexed, and incubated for 14-18 hours at 50° C. The 40 and 100 kDa protein solutions were mixed individually with an equal volume of the warmed 20 mg/ml RBBR stock, vortexed, and incubated for 14-18 hours at 50° C. Following incubation, solutions were removed from the waterbath, allowed to equilibrate to room temperature, filtered through a 0.8 µm cameo filter to remove any residual particulate, and stored at 4° C. until use.

To provide a low molecular weight standard, aprotinin was prepared at a concentration of 11 mg/ml in 140 mM sodium phosphate, 80 mM sodium chloride, 3% (w/v) SDS. The solution was gently vortexed and warmed to 50° EC for 15 minutes. After warming, 5.7 mg of RBBR/ml was added to the solution, and the solution was then mixed and incubated for 40 minutes at 70° C. β-mercaptoethanol was then added (6.9 µl/ml), and the solution was again mixed and incubated for an additional 10 minutes at 70° C., after which 9.1 µl/ml of acrylonitrile was added. The solution was mixed, incubated for 30 minutes at room temperature, and then filtered through a 0.8 µm cameo filter cartridge and stored at 4° C.

Eosin Isothiocyanate Labeling of the 50 kDa Protein

The 8 $A_{280}$/ml 50 kDa stock in 1% $SDS/H_2O$ was combined with an equal volume of 280 mM sodium phosphate, 160 mM sodium chloride, 1% (w/v) SDS, pH 9.7 buffer, mixed, and warmed for 15 minutes at 50° C. A 70 mg/ml stock of eosin isothiocyanate (EITC) was prepared in dimethylformamide immediately before use, and a sufficient volume of this solution was added to the 50 kDa protein solution to achieve a final concentration of 7 mg/ml EITC. The solution was then mixed, incubated at 50° C. for 14-18 hours in the dark, equilibrated to room temperature, filtered through a 0.8 µm cameo filter cartridge, and stored in the dark at 4° C.

Preparation of Final Mixture

The quality of the labeling was assessed by running each protein stock on SDS-PAGE (Laemmli, E. K., *Nature* 227: 680-685 (1970)), then preparing a mix of all of the proteins so that the amounts of the proteins produce bands which appear visually to have equivalent intensities. The mix was then diafiltered using a 3,000 molecular weight cutoff mini-ultrasette unit with 10% glycerol, 50 mM TRIS, 5 mM EDTA (to enhance stability of the preparation upon storage), pH 6.8 buffer. A Sephadex G-25 column was used to remove a small amount of unreacted dye which remained after diafiltration. The Sephadex column that was equilibrated with 50 mM Tris, 1% (w/v) SDS, 5 mM EDTA, pH 6.8, and the column size was 15 times the volume of the sample. SDS-PAGE was carried out on the final mixture to assess the quality of the mix.

Example 1

Cloning and Expression of a 10 kD Protein

The initial objective was to make a protein molecular weight standard ranging from 10 kD-250 kD with 10 kD increments. Therefore, a modified portion of T4 gene 32 protein containing 87 amino acids (261 bp) that includes 6 histidine residues at the carboxy end (FIG. 1; SEQ ID NO:1) (see U.S. Pat. No. 5,449,758) was used. The fragment was cloned and expressed to produce a 10 kD protein. The clone was designated as plasmid pTrcprl-monomer. This construct contains an unique AvaI site (CTCGGG) to generate multimers of any given AvaI fragment with CTCGGG sequence. When digested with AvaI, the clone generates a TCGG overhang. Thus, when a DNA fragment having a TCGG overhang at both ends is ligated with AvaI-digested pTrcprl-monomer, the fragment will be ligated only in one direction (head-to-tail). Using proper ligation condition, it was possible to generate multimers of a desired fragment. For example, if a single AvaI fragment (264 bp) is ligated to pTrcprl-monomer it will produce a 20 kD protein; if two fragments are ligated, it will produce a 30 kD protein; and so on.

As noted above, the pTrcprl-monomer was designed to produce a 10 kD protein. However, the induced or uninduced cultures did not produce any 10 kD protein. Interestingly, the larger clones with multiple inserts produced proteins of expected sizes. The level of expression, however, varied among the clones depending on the number of inserts. The level of expression of various proteins (in kD) was as follows:
20<30<40<50<60<70≅80≅90≅100≅120>160>180>200>220>250.

To obtain a protein of low molecular weight for use in the production of molecular weight standards, natural proteins close to 10 kD in size that are well-expressed in *E. coli* were sought. One such protein is thioredoxin, which consists of 108 amino acids and which has a molecular mass of 12 kD (Lunn et al., *J. Biol. Chem.* 259:10469-10474 (1984); Hoog et al., *BioSci Rep.* 4:917-923 (1984)). Thioredoxin is ubiquitously distributed, and is present in an unusually high concentration per cell (10,000-20,000 molecules/cell). In addition, it has also been shown that when overexpressed, it represents almost 40% of the total soluble cellular protein (Lunn et al., Id.). It thus appeared that thioredoxin might be a suitable candidate for the production of a 10 kD protein if a 2 kD portion was deleted from its carboxy terminus. One such construct (pTrxfusprl10A) which produced a 10 kD protein contained: a) amino acids 1-85 from thioredoxin; b) a substitution of glutamic acid for valine at amino acid position number 86; and c) histidine residues at positions 87-92. This truncated thioredoxin construct produced about 20-30% of the total cellular protein. However, unlike full length thioredoxin this construct produced almost all of the induced protein as inclusion bodies. In other experiments, 33 of the 108 amino acids were deleted from the thioredoxin carboxy terminus; such constructs also produced almost all of the induced protein as inclusion bodies upon expression in the host cells. It may also be possible to produce polypeptides by the present methods using truncated thioredoxin in which 2-22 amino acids have been deleted from the carboxy terminus, or in which 33-50 amino acids have been deleted, as described above. Following expression of the protein in the host cells, the inclusion bodies were easily isolated from the host cells by centrifugation.

Example 2

Cloning of Fusion Proteins Larger than 10 kD

In order to make fusion protein with truncated thioredoxin, a vector containing a unique AvaI site, used to make concatamers, was developed; this vector was designated pTrxA-concat (FIG. 4; SEQ ID NO:8). Using this vector, a series of fusion proteins has been made linking the vector to single or multiple fragments of thioredoxin (FIG. 5; SEQ ID NO:11) (thioredoxin-thioredoxin fusion), *E. coli* DEAD-box protein (FIG. 6; SEQ ID NO:14), KpnI methylase (FIG. 7; SEQ ID NO:17), or 264-bp modified T4 gene 32 protein (FIG. 1; SEQ ID NO:1) (See U.S. Pat. No. 5,449,758).

Specifically, fusion proteins of the indicated molecular weights were made by ligating pTrxA-concat to one or more copies of the nucleic acid molecules encoding 10 kD fragments of truncated *E. coli* thioredoxin (ΔtrxA) or T4 gene 32 protein, or 5 kD fragments of *E. coli* Dead-Box protein or KpnI methylase, as shown in Table 1. In all cases, the fusion protein was expressed as inclusion bodies. Thus, using the methods of the present invention, polypeptides ranging in size from 10 kD to 220 kD, in 5-10 kD increments, have been efficiently produced as inclusion bodies.

TABLE 1

Scheme for Production of Fusion Proteins over a Range of Molecular Weights.

| | Number of Copies of Gene Ligated to Vector | | | |
|---|---|---|---|---|
| Molecular Weight (kD) | 10 kD)trxA | 5 kD Dead-Box Protein | 10 kD T4 Gene 32 Protein | 5 kD KpnI Methylase |
| 10 | 1 | 0 | 0 | 0 |
| 15 | 1 | 1 | 0 | 0 |
| 20 | 1 | 2 | 0 | 0 |
| 25 | 1 | 0 | 0 | 3 |
| 30 | 3 | 0 | 0 | 0 |
| 40 | 1 | 0 | 3 | 0 |
| 50 | 1 | 0 | 4 | 0 |
| 50 | 5 | 0 | 0 | 0 |
| 60 | 6 | 0 | 0 | 0 |
| 70 | 1 | 0 | 6 | 0 |
| 80 | 8 | 0 | 0 | 0 |
| 90 | 9 | 0 | 0 | 0 |
| 100 | 1 | 0 | 9 | 0 |
| 120 | 1 | 0 | 11 | 0 |
| 160 | 1 | 0 | 15 | 0 |
| 220 | 1 | 0 | 21 | 0 |

Example 3

Production of Unstained Protein Molecular Weight Ladders

To demonstrate its utility, the present system was used to make unstained protein molecular weight ladders. Purified proteins of differing sizes, made as described in Example 2, were mixed and separated by SDS-PAGE, and the banding patterns in various acrylamide concentrations was observed.

The results of these experiments showed the combination of proteins allowing the best resolution over a range of acrylamide concentrations to be a mixture of 10 kD, 15 kD, 20 kD, 25 kD, 30 kD, 40 kD, 50 kD, 60 kD, 70 kD, 80 kD, 90 kD, 100 kD, 120 kD, 160 kD and 220 kD proteins. These results demonstrate that the methods of the present invention are useful in making proteins of various size ranges, and may be used to produce compositions comprising protein molecular weight ladders.

Example 4

Production of Prestained Protein Molecular Weight Ladders

Prestained protein molecular weight ladders have been commercially available for more than 10 years in two distinct forms. In one form, all of the proteins are stained with a single dye, and in the second form each protein is stained with different dyes (a multicolored version). These two distinct forms have several advantages and disadvantages. Single color markers, for example, are typically prepared in a way that results in relatively sharp bands in SDS-PAGE compared to multicolored markers, but directly relating each band to its corresponding molecular weight can be difficult since the only point of reference in single colored prestained markers is the highest or lowest molecular weight band. If either of these reference bands disappears during storage, or is not resolved on the gel, the absence of a point of reference makes identification of the remaining bands difficult. Similarly, determination of the identity of the bands in multicolored markers is easy since each band is a distinct color, but some of the bands are very broad in SDS-PAGE and some of the colors are difficult to detect visually.

In the present invention, a new set of prestained protein molecular weight markers has been developed. These markers are evenly spaced on SDS-PAGE and comprise a reference band of a different color from the other bands to allow easy orientation of all of the marker bands. A single dye was used to stain all but one protein (the reference protein), which was stained with a second dye. Staining protocols were developed to produce prestained proteins that gave sharp bands on SDS-PAGE using both dyes, in contrast to the wide variations in band sharpness common in multicolored markers. The protein stained with the second dye serves as a point of reference within the marker facilitating the identification of the prestained marker bands. A number of dyes were tested including Remasol brilliant blue R (RBBR), eosin isothiocyanate, procion red, reactive orange (also known as procion yellow), eosin iodoacetamide, reactive black 5, Remasol brilliant violet 5R, reactive orange 14, rhodamine isothiocyanate, and malachite green isothiocyanate. Labeling and storage conditions of each protein component was optimized in terms of buffer pH and ionic composition, dye concentration, protein concentration, temperature of labeling, and incubation time during labeling, as described in detail above in the Materials and Methods section.

Figure 8:
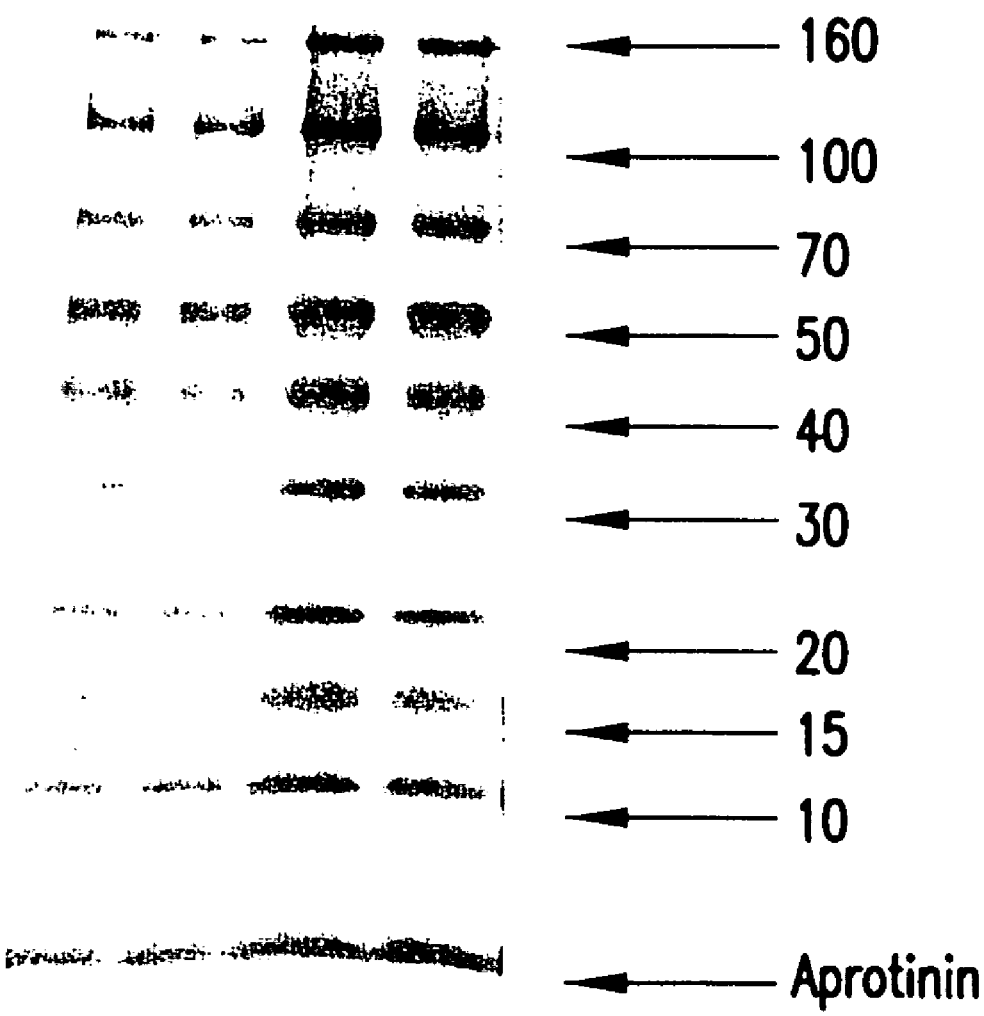
FIG. 8 is a photograph of a 4-20% SDS-PAGE gradient gel of four different load volumes of the prestained molecular weight markers, demonstrating the 50 kD reference band stained with eosin isothiocyanate and the remaining bands in the ladder stained with RBBR.

A number of different cloned proteins were labeled with RBBR and then run on SDS-PAGE to determine the effectiveness of the labeling procedure and to determine the apparent molecular weights of the labeled proteins. As shown in FIG. 8, the most intense staining and most even spacing on SDS-PAGE were achieved with the combination of 10, 15, 20, 30, 40, 50, 70, 100, and 160 kDa proteins. The 50 kDa protein was labeled with eosin isothiocyanate so that a highlight or reference band could be incorporated into the marker ladder. This bright pink band was positioned as the fourth band from the top and the sixth band from the bottom (not including the aprotinin standard which is not part of the ladder composition), providing an easy point of reference to determine the molecular weight of a particular band. These results demonstrate that the present methods may be used to produce molecular weight marker sets that are easily prestained.

Example 5

Production of Molecular Weight Markers for Use in Blotting

It would be useful to have molecular weight markers that can not only be used to determine molecular weight after coomassie blue staining in a gel, but that also could be used as molecular weight markers following membrane transfer techniques such as western blotting. The molecular weight markers produced by the present methods can be used for both of these applications. As described above, each of the protein components in the unstained molecular weight marker mixture contains six histidine residues at the carboxy terminus. Since these six histidine residues interact with $Ni^{++}$ (Hochuli, E., and Piesecki, S., *Methods: A Companion to Methods in Enzymology* 4:68-72 (1992), a Ni-NTA-alkaline phosphatase conjugate along with nitroblue tetrazolium chloride (NBT)/5-bromo-4-chloro-3-indolylphosphate p-toluidine salt (BCIP) can be used to detect and identify the protein components in a Western Blot.

Example 6

Production of Small or Toxic Proteins

The present system is particularly useful to express proteins that are difficult to express in *E. coli*, whether this difficulty is due to (1) smaller size of the protein (in general, smaller proteins are expressed at lower levels in *E. coli*); (2) toxicity of the heterologous protein to the *E. coli* host; (3) inefficient translation in *E. coli*; or (4) instability of the mRNA. As shown in the examples above, the present methods allow efficient production of heterologous proteins as inclusion bodies. Since inclusion bodies are an isolated form of the expressed protein, this system may be used to produce toxic proteins or small peptides which otherwise might not be produced in *E. coli* or other bacterial host cells. Using this system, peptides of 5 kD and smaller have been produced. The system can also be used to produce polypeptides 250 kD in size or larger.

Example 7

Optimization of Conditions for Labeling Protein Ladders with Remasol Brilliant Blue R (RBBR)

In general, chemical modification or conjugation of a protein (e.g., labeling it with a dye) involves the reaction of functionally reactive groups on the protein with corresponding functionally reactive groups on the label. Reactive groups able to couple with amine-containing molecules, such as proteins containing lysine residues, are by far the most common functional groups present on cross-linking reagents such as dyes. An amine-coupling process therefore can be used to conjugate nearly all proteins or peptides with other molecules.

In the present invention, a variety of dyes, including remazol brilliant blue R (RBBR) and eosin isothiocyanate, have been used as coupling reagents for labeling of molecular weight ladder proteins. These dyes primarily react with nucleophilic amine groups on the proteins to yield stable protein-dye complexes. The dyes can also react, to some extent, with other nucleophiles on the target proteins, such as sulfhydryl groups and phenolate ions of tyrosine side chains.

To produce the most useful (i.e., highest color intensity and band sharpness) and consistent (i.e., lowest variability in band mobility between batches) prestained protein ladders, it is essential to optimize the staining protocol. The band intensity will depend upon the amount of primary amine groups present in the protein being conjugated with the dye, while the band sharpness will depend upon how many of the available primary amines in the target protein have been conjugated with the dye. Each of these variables will be dependent upon the environmental conditions to which the protein and dye are subjected during conjugation. Thus, the extent of conjugation of the target marker proteins with dye will depend upon a number of conditions during staining, including concentrations of the protein and dye in solution, pH of the solution, ionic conditions, temperature, and duration of incubation of protein with the dye.

Thus, one object of the present invention is to develop conditions to stain protein molecular weight markers that will provide molecular weight ladders with bands that resolve as intensely, as homogeneously, and as consistently as possible. To meet this objective, the labeling conditions in terms of concentrations of the protein and dye in solution, pH of the solution (adjusted prior to addition of protein(s) and dye(s)), and temperature and time of incubation, were optimized.

To minimize volumes in which the reactions were carried out, varied concentrations of proteins were examined. Proteins produced as described above were prepared in solutions at 1, 2, and 4 $A_{280}$ units/ml, and labeled with RBBR as generally described above in the Materials and Methods section, and then separated on 4-20% SDS-PAGE gradient gels as above in Example 4. Intensity of staining was then determined by densitometry and by eyesight. In general, protein concentrations of 1 and 2 $A_{280}$ units/ml produced signals of similar intensity, while labeling intensity was lower at 4 $A_{280}$ units/ml.

In analogous experiments, the optimal concentration of RBBR was determined by staining proteins with RBBR at a range of concentrations from 0.3 to 30 mg/ml. In general, 10 mg/ml RBBR was found to provide the most intensely staining, homogeneous product when proteins of 40 kD and 100 kD were labeled, while proteins of 10 kD, 15 kD, 20 kD, 30 kD, 45 kD, 50 kD, 60 kD, 70 kD, and 160 kD, were optimally labeled by 30 mg/ml of RBBR. These results suggest that a range of about 5-50 mg/ml, or 10-30 mg/ml, of RBBR may be optimal for labeling of protein molecular weight ladders consisting of proteins of varying molecular weights.

In preliminary experiments designed to determine optimal temperature and time periods for labeling, incubation of the proteins in solution without dye indicated that the proteins tended to degrade when incubated at 70° C. for 0.5-1 hour, and when incubated at 60° C. for about 2-5 hours. When incubated overnight (12-24 hours) at about 50° C. or lower, however, the proteins appeared to be stable (i.e., to resist degradation in solution). Upon staining the protein solutions with RBBR at the above-noted concentration ranges, the most homogeneous and intense bands (i.e., sharpest and brightest banding patterns) were observed in protein preparations stained with RBBR overnight at 50EC. Shorter incubation periods (e.g., 4 to 8 hours) produced more heterogeneous (i.e., more diffuse and less intense) banding patterns, particularly with lower molecular weight proteins (10 kD to 60 kD). Overnight incubations at room temperature (about 20° C. to 25° C.) and at 37° C. did not produce satisfactory results; protein ladder preparations stained with RBBR under these conditions resulted in ladders demonstrating even more diffuse and less intense banding patterns. These results indicate that overnight staining of proteins at 50° C. is optimal for producing protein molecular weight ladders prestained with RBBR.

Finally, to determine pH optima for staining of the ladder preparations with RBBR, proteins were labeled with RBBR as above in solutions buffered to pHs ranging from about 7.2 to about 9.7. Ideal results (i.e., most intensely staining and least diffuse banding patterns) were observed in solutions buffered to pH 9.2. It is to be noted, however, that the pH of the final staining mixture was about 8.3 (after addition of protein and dye), while the optimal initial pH of the buffer to which protein and dye were added was about 9.2.

Taken together, these results suggest that the optimal conditions for producing protein molecular weight ladders prestained with RBBR include a protein concentration of about 1 to 2 $A_{280}$ units/ml, a dye concentration of about 5 to about 50 mg/ml, a pH of about 9.0 to 9.5, and incubation of the protein and dye for about 12-24 hours at a temperature of about 50° C.

Example 8

Optimization of Conditions for Labeling Protein Ladders with Eosin Isothiocyanate As noted in Example 4 above, eosin labeling of a single protein band in a complex protein molecular weight ladder, particularly between the RBBR-labeled 40 kD and 70 kD bands, provides a valuable reference band that permits rapid and accurate identification of all of the other protein bands in the ladder. Therefore, the optimal conditions for labeling 30 kD, 40 kD, 50 kD and 60 kD proteins with eosin isothiocyanate, for use in the ladders of the invention, were determined.

Various preparations of 30 kD, 40 kD, 50 kD and 60 kD recombinant proteins, prepared as described above in Examples 1 and 2, were incubated with eosin isothiocyanate under the conditions of protein concentration, dye concentration, temperature, time, and pH, used for the studies with RBBR in Example 7. Following labeling with eosin isothiocyanate, protein preparations were run on 4-20% SDS-PAGE.

As shown in FIGS. 9-12, the pH and temperature conditions used during eosin labeling of 30 kD, 40 kD, 50 kD and 60 kD reference proteins dramatically affected the intensity of staining and sharpness of resolution of the bands on SDS-PAGE. Optimal results were obtained when about 2 $A_{280}$ units of the 50 kD protein were incubated overnight (ideally for about 4-16 hours) at 50° C. with a final concentration of eosin isothiocyanate of about 7 mg/ml at pH 9.2 (see FIG. 9, lane 5; FIG. 10, lane 13; FIG. 11, lane 14; and FIG. 12, lane 8), and when the 60 kD protein was labeled under the same conditions, except at pH 9.2-9.7 (see FIG. 9, lane 13, and FIG. 12, lane 6). Under these same conditions, however, incubation of the proteins with the commonly used dye procion red produced little or no staining of the ladder bands (see FIG. 12, lanes 1-4).

Example 9

Optimization of Conditions for Labeling Protein Ladders with Malachite Green Isothiocyanate To provide reference bands and proteins ladders stained with a variety of colors, it would be advantageous to stain the protein ladders of the invention with a dye, such as malachite green, of different color from RBBR and eosin. Therefore, the optimal conditions for labeling 30 kD, 40 kD, 50 kD and 60 kD proteins with malachite green isothiocyanate were determined.

Various preparations of 30 kD, 40 kD, 50 kD and 60 kD recombinant proteins, prepared as described above in Examples 1 and 2, were incubated with malachite green isothiocyanate under the conditions of protein concentration, dye concentration, temperature, time, and pH, used for the studies with RBBR in Example 7 and with eosin isothiocyanate in Example 8. Following labeling with malachite green isothiocyanate, protein preparations were run on 4-20% SDS-PAGE.

As shown in FIG. 13, the pH conditions used during malachite green labeling of 40 kD, 50 kD and 60 kD reference proteins dramatically affected the intensity of staining and sharpness of resolution of the bands on SDS-PAGE. Optimal results were obtained when about 1-2 $A_{280}$ units of the proteins were incubated overnight (ideally for about 16 hours) at room temperature with a final concentration of malachite green isothiocyanate of about 20-30 mg/ml at pH 9.2 (see FIG. 13, lanes 2, 4, 6 and 8).

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method for making a stained molecular weight marker, the method comprising:
   (1) producing a first thioredoxin polypeptide comprising thioredoxin, a modified thioredoxin, or a truncated thioredoxin; and
   (2) incubating the first thioredoxin polypeptide with a protein-binding dye to form a first stained molecular weight marker.

2. The method of claim 1, wherein the incubating step is incubating the first thioredoxin polypeptide with a protein-binding dye to form a first stained molecular weight marker that has a molecular weight of between 5 kD and 330 kD.

3. The method of claim 1, further comprising:
   (3) admixing the thioredoxin polypeptide with a plurality of stained polypeptides of different molecular weights to form a plurality of pre-stained molecular weight markers.

4. The method of claim 3, wherein the admixing step is admixing the thioredoxin polypeptide with a plurality of stained polypeptides of different molecular weights to form a plurality of pre-stained molecular weight markers having molecular weights of between 5 kD and 330 kD.

5. The method of claim 3, wherein the admixing step is admixing the thioredoxin polypeptide with a plurality of stained polypeptides of different molecular weights to form a plurality of pre-stained molecular weight markers having a molecular weights between 10 kD and 250 kD.

6. The method of claim 3, wherein the admixing step is admixing the thioredoxin polypeptide with a plurality of stained polypeptides of different molecular weights to form a pre-stained molecular weight ladder that comprises from 3-20 proteins of different sizes.

7. The method of claim 3, wherein the admixing step is admixing the thioredoxin polypeptide with a plurality of stained polypeptides of different molecular weights to form a pre-stained molecular weight ladder comprising at least one protein of a molecular weight of from 10 kD to 50 kD.

8. The method of claim 3, wherein the admixing step is admixing the thioredoxin polypeptide with a plurality of stained polypeptides of different molecular weights to form a pre-stained molecular weight ladder comprising at least one protein of a molecular weight of from 50 kD to 100 kD.

9. The method of claim 3, wherein the admixing step is admixing the thioredoxin polypeptide with a plurality of stained polypeptides of different molecular weights to form a pre-stained molecular weight ladder that comprises at least one protein of a molecular weight of from about 100 kD to about 220 kD.

10. The method of claim 3, wherein admixing is admixing the thioredoxin polypeptide with a plurality of stained polypeptides of different molecular weights to form a pre-stained molecular weight ladder that comprises two or more proteins having molecular weight increments of 5 kD, 10 kD, 20 kD, 25 kD, 50 kD, or 100 kD.

11. The method of claim 3, wherein admixing is admixing the thioredoxin polypeptide with a plurality of stained polypeptides of different molecular weights to form a pre-stained molecular weight ladder that comprises two or more proteins having molecular weight increments of 10 kD.

12. The method of claim 3, wherein admixing is admixing the thioredoxin polypeptide with a plurality of stained polypeptides of different molecular weights to form a pre-stained molecular weight ladder that comprises at least three proteins having molecular weight increments of 10 kD or a multiple thereof.

13. The method of claim 1, wherein the producing step comprises producing a first thioredoxin polypeptide comprising an *E. coli* thioredoxin.

14. The method of claim 1, wherein the producing step comprises producing a first thioredoxin polypeptide comprising a modified thioredoxin.

15. The method of claim 14, wherein the producing step comprises producing a first thioredoxin polypeptide comprising a modified thioredoxin having the ability to form inclusion bodies upon expression in a bacterial host cell.

16. The method of claim 1, wherein the producing step comprises producing a first thioredoxin polypeptide comprising a truncated thioredoxin.

17. The method of claim 16, wherein the producing step comprises producing a first thioredoxin polypeptide comprising a carboxy terminal-truncated thioredoxin.

18. The method of claim 16, wherein the producing step comprises producing a first thioredoxin polypeptide comprising a thioredoxin having a truncation of between 2 and 50 carboxy terminal amino acids.

19. The method of claim 16, wherein the producing step comprises producing a first thioredoxin polypeptide having a molecular weight of 10 kD.

20. The method of claim 16, wherein the producing step comprises producing a first thioredoxin polypeptide comprising a thioredoxin having a carboxy terminal-truncated form of *Escherichia coli* thioredoxin which is encoded by a nucleic acid molecule having a nucleotide sequence as set forth in SEQ ID NO:8.

21. The method of claim 1, wherein the producing step results in production of a first thioredoxin polypeptide that comprises a multimer of thioredoxin, a modified thioredoxin, or a truncated thioredoxin.

22. The method of claim 21, wherein the producing step results in production of the first thioredoxin polypeptide, wherein the first thioredoxin polypeptide comprises a multimer of a truncated thioredoxin.

23. The method of claim 21, wherein the producing step results in production of a first thioredoxin polypeptide that has a molecular weight of between 20 kD and 250 kD.

24. The method of claim 1, wherein the producing step results in production of a first thioredoxin polypeptide that comprises a fusion of thioredoxin, a modified thioredoxin, or a truncated thioredoxin and another polypeptide.

25. The method of claim 24, wherein the producing step results in production of a first thioredoxin polypeptide that has a molecular weight of between 15 kD and 220 kD.

26. The method of claim 1, further comprising:
(3) producing a second thioredoxin polypeptide comprising thioredoxin, a modified thioredoxin, or a truncated thioredoxin; and
(4) incubating the second thioredoxin polypeptide with a protein-binding dye to form a second stained molecular weight marker.

27. The method of claim 26, wherein said second stained molecular weight marker has a molecular weight of between 5 kD and 300 kD.

28. The method of claim 26, wherein the producing step results in production of the second thioredoxin polypeptide, wherein the second thioredoxin polypeptide comprises a multimer of thioredoxin, a modified thioredoxin, or a truncated thioredoxin.

29. The method of claim 26, wherein the second polypeptide is admixed with the first polypeptide to form a molecular weight marker set.

30. The method of claim 29, wherein the pre-stained molecular weight marker set comprises proteins having molecular weights of between 5 kD and 330 kD.

31. The method of claim 29, wherein the pre-stained molecular weight marker set comprises proteins having molecular weights between 10 kD and 250 kD.

32. The method of claim 26, further comprising:
(5) producing a third thioredoxin polypeptide comprising thioredoxin, a modified thioredoxin, or a truncated thioredoxin; and
(6) incubating the third thioredoxin polypeptide with a protein-binding dye to form a third stained molecular weight marker.

33. The method of claim 32, wherein said third stained molecular weight marker has a molecular weight of between 5 kD and 330 kD.

34. The method of claim 32, wherein the producing step results in production of the third thioredoxin polypeptide that comprises a multimer of thioredoxin, a modified thioredoxin, or a truncated thioredoxin.

35. The method of claim 32, wherein the third polypeptide is admixed with the first polypeptide and the second polypeptide to form a molecular weight marker set.

36. The method of claim 35, wherein the pre-stained molecular weight marker set comprises proteins having molecular weights of between 5 kD and 330 kD.

37. The method of claim 35, wherein the pre-stained molecular weight marker set comprises proteins having molecular weights of between 10 kD and 250 kD.

38. A pre-stained molecular weight marker comprising thioredoxin, a modified thioredoxin, or a truncated thioredoxin.

39. The pre-stained molecular weight marker of claim 38, wherein the molecular weight marker has a molecular weight of between 5 kD and 330 kD.

40. A molecular weight marker set comprising a plurality of pre-stained molecular weight markers, wherein at least two of the stained molecular weight markers comprise thioredoxin, a modified thioredoxin, or a truncated thioredoxin.

41. The molecular weight marker set of claim 40, wherein the plurality of pre-stained molecular weight markers have molecular weights of between 5 kD and 330 kD.

* * * * *

SEQUENCE LISTING (1) GENERAL INFORMATION:

(iii) NUMBER OF SEQUENCES: 17

(2) INFORMATION FOR SEQ ID NO: 1:

(i) SEQUENCE CHARACTERISTICS:
        (A) LENGTH: 270 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 1:

```
CTCGGGTACA ACACTGACAA TAAAGAGTAC GTTCTTGTTA AACTTAAGGG TTTTTCTTCT      60

GAAGATAAAG GCGAGTGGAA ACTGAAACTC GATAATGCGG GTAACGGTCA AGCAGTAATT     120

CGTTTTCTTC CGTCTAAAAA TGATGAACAA GCACCATTCG CAATTCTTGT AAATCACGGT     180

TTCAAGAAAA ATGGTAAATG GTATATTGAA ACATCATCTA CCCATGATTA CGATTCTCCA     240

GTACAATACA TCAGTAAAAA TGATCTCGGG                                     270
```

(2) INFORMATION FOR SEQ ID NO: 2:

(i) SEQUENCE CHARACTERISTICS:
        (A) LENGTH: 263 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 2:

```
CCATGGGTTT TTCTTCTGAA GATAAAGGCG AGTGGAAACT GAAACTCGAT AATGCGGGTA      60

ACGGTCAAGC AGTAATTCGT TTTCTTCCGT CTAAAAATGA TGAACAAGCA CCATTCGCAA     120

TTCTTGTAAA TCACGGTTTC AAGAAAAATG CTAAATGGTA TATTGAAACA TCATCTACCC     180

ATGATTACGA TTCTCCAGTA CAATACATCA GTAAAAATGA TCTCGGGTAC AACACTGACA     240

ATAAACACCA CCACCACCAC CAC                                             263
```

(2) INFORMATION FOR SEQ ID NO: 3:

(i) SEQUENCE CHARACTERISTICS:
        (A) LENGTH: 22 base pairs
        (B) TYPE: nucleic acid

```
        (C) STRANDEDNESS: both
        (D) TOPOLOGY: both (ii) MOLECULE TYPE: cDNA (xi) SEQUENCE DESCRIPTION: SEQ ID NO: 3:

AGGAAATACT TACATATGAG CG                                              22

(2) INFORMATION FOR SEQ ID NO: 4:

(i) SEQUENCE CHARACTERISTICS:
        (A) LENGTH: 56 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 4:

TATTACTGCA GTTAGTGGTG GTGGTGGTGG TGTTCACCGT TTTTGAACAG CAGCAG         56

(2) INFORMATION FOR SEQ ID NO: 5:

(i) SEQUENCE CHARACTERISTICS:
        (A) LENGTH: 280 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 5:

CATATGAGCG ATAAAATTAT TCACCTGACT GACGACAGTT TTGACACGGA TGTACTCAAA     60

GCGGACGGGG CGATCCTCGT CGATTTCTGG GCAGAGTGGT GCGGTCCGTG CAAAATGATC    120

GCCCCGATTC TGGATGAAAT CGCTGACGAA TATCAGGGCA AACTGACCGT TGCAAAACTG    180

AACATCGATC AAAACCCTGC TCACTGCGCC GAAATATGGC ATCCGTGGTA TCCCGACTCT    240

GCTGCTGTTC AAAAACGGTG AACACCACCA CCACCACCAC                          280

(2) INFORMATION FOR SEQ ID NO: 6:

(i) SEQUENCE CHARACTERISTICS:
        (A) LENGTH: 36 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 6:

TAATAACCAT GGCATATGAG CGATAAAATT ATTCAC                               36

(2) INFORMATION FOR SEQ ID NO: 7:

(i) SEQUENCE CHARACTERISTICS:
        (A) LENGTH: 36 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 7:

ATTATACCCG AGTCCACCAC GGATGCCATA TTTCGG                               36

(2) INFORMATION FOR SEQ ID NO: 8:
```

```
    (i) SEQUENCE CHARACTERISTICS:
        (A) LENGTH: 280 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 8:

CCATGCTCAT ATGAGCGATA AAATTATTCA CCTGACTGAC GACAGTTTTG ACACGGATGT      60

ACTCAAAGCG GACGGGGCGA TCCTCGTCGA TTTCTGGGCA GAGTGGTGCG GTCCGTGCAA     120

AATGATCGCC CCGATTCTGG ATGAAATCGC TGACGAATAT CAGGGCAAAC TGACCGTTGC     180

AAAACTGAAC ATCGATCAAA ACCCTGGCAC TGCGCCGAAA TATGGCATCC GTGGTGGACT     240

CGGGTACAAC ACTGACAATA AACACCACCA CCACCACCAC                          280

(2) INFORMATION FOR SEQ ID NO: 9:

(i) SEQUENCE CHARACTERISTICS:
        (A) LENGTH: 33 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 9:

TAATAACTCG GGAGCGATAA AATTATTCAC CTG                                  33

(2) INFORMATION FOR SEQ ID NO: 10:

(i) SEQUENCE CHARACTERISTICS:
        (A) LENGTH: 33 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 10:

ATAATACCCG AGTTTGGTTG CCGCCACTTC ACC                                  33

(2) INFORMATION FOR SEQ ID NO: 11:

(i) SEQUENCE CHARACTERISTICS:
        (A) LENGTH: 282 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 11:

CTCGGGAGCG ATAAAATTAT TCACCTGACT GACGACAGTT TTGACACGGA TGTACTCAAA      60

GCGGACGGGG CGATCCTCGT CGATTTCTGG GCAGAGTGGT GCGGTCCGTG CAAAATGATC     120

GCCCCGATTC TGGATGAAAT CGCTGACGAA TATCAGGGCA AACTGACCGT TGCAAAACTG     180

AACATCGATC AAAACCCTGG CACTGCGCCG AAATATGGCA TCCGTGGTAT CCCGACTCTG     240

CTGCTGTTCA AAAACGGTGA AGTGGCGGCA ACCAAACTCG GG                       282

(2) INFORMATION FOR SEQ ID NO: 12:

(i) SEQUENCE CHARACTERISTICS:
        (A) LENGTH: 34 base pairs
```

(B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 12:

TAATAACTCG GGAAGCTGAC TAATCCGGAA GTAG                                   34

(2) INFORMATION FOR SEQ ID NO: 13:

(i) SEQUENCE CHARACTERISTICS:
        (A) LENGTH: 33 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 13:

ATTATTCCCG AGCAGTGCGC GGTATTGATC CAG                                    33

(2) INFORMATION FOR SEQ ID NO: 14:

(i) SEQUENCE CHARACTERISTICS:
        (A) LENGTH: 138 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 14:

CTCGGGAAGC TGACTAATCC GGAAGTAGAA CTGCCGAACG CAGAACTGCT AGGCAAACGC       60

CGTCTGGAAA AATTCGCCGC TAAAGTACAG CAGCAGCTGG AAAGCAGCGA TCTGGATCAA      120

TACCGCGCAC TGCTCGGG                                                    138

(2) INFORMATION FOR SEQ ID NO: 15:

(i) SEQUENCE CHARACTERISTICS:
        (A) LENGTH: 35 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 15:

GATTACTCGG GGCACATAAA ATGCTAAAAG ATACA                                  35

(2) INFORMATION FOR SEQ ID NO: 16:

(i) SEQUENCE CHARACTERISTICS:
        (A) LENGTH: 35 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 16:

TCTAACCCGA GTAAGATCGT TTTTCTTGAA CCACC                                  35

(2) INFORMATION FOR SEQ ID NO: 17:

(i) SEQUENCE CHARACTERISTICS:
        (A) LENGTH: 405 base pairs (B) TYPE: nucleic acid
(C) STRANDEDNESS: both
(D) TOPOLOGY: both (ii) MOLECULE TYPE: cDNA (xi) SEQUENCE DESCRIPTION: SEQ ID NO: 17:

```
CTCGGGGCAC ATAAAATGCT AAAAGATACA GGCATTATTG CTATCAGCAT TGATGACTAT      60

GAATTTGCTC ATTTAAAAAT ACTGATGGAT AAAATTTTCG GTGAAGATAA TTTCATCGGA     120

AATATCGTCG TTTGTCGTTC AAAAAATGGA AAAGTGAGCA AGCGAAATAT AGCGTCTGCT     180

CATGAATATT TACTGGTTTA TGGAAAATCA GATATGGCGG AACTATCTGG ACAACCAGAT     240

GATAAATCTC TTTATGATAA AGTTGATTGT TTTGGTGAAT ATAGAATTGA CGGAATGTTC     300

AGAAAAAAAG GTGATTCAAG TTTGAGAACT GATCGCCCTA ATATGTTTTA TCCTTTATAT     360

TTTAACCCAT CAACAGGTGA AGTACAGGTA GAGCCAGAAC TCGGG                     405
```